(12) United States Patent
Shelton, IV

(10) Patent No.: US 8,496,632 B2
(45) Date of Patent: Jul. 30, 2013

(54) SURGICAL ACCESS DEVICE WITH ADJUSTABLE CANNULA

(75) Inventor: Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 13/217,927

(22) Filed: Aug. 25, 2011

(65) Prior Publication Data

US 2013/0053777 A1    Feb. 28, 2013

(51) Int. Cl.
*A61M 25/00* (2006.01)

(52) U.S. Cl.
USPC .......................................................... 604/264

(58) Field of Classification Search
USPC .................. 604/164.04, 164.11, 264, 506, 216
See application file for complete search history.

(56) References Cited

U.S. PATENT DOCUMENTS

| | | | | |
|---|---|---|---|---|
| 5,250,026 A | * | 10/1993 | Ehrlich et al. | 604/60 |
| 5,368,046 A | * | 11/1994 | Scarfone et al. | 600/567 |
| 5,505,710 A | * | 4/1996 | Dorsey, III | 604/158 |
| 5,746,720 A | * | 5/1998 | Stouder, Jr. | 604/117 |
| 5,882,344 A | * | 3/1999 | Stouder, Jr. | 604/264 |
| 6,197,002 B1 | * | 3/2001 | Peterson | 604/164.01 |
| 6,989,003 B2 | * | 1/2006 | Wing et al. | 604/161 |
| 7,798,998 B2 | | 9/2010 | Thompson et al. | |
| 7,806,870 B2 | * | 10/2010 | Mastri et al. | 604/164.04 |
| 7,828,775 B2 | * | 11/2010 | Okoniewski | 604/167.01 |
| 8,137,267 B2 | * | 3/2012 | Shelton et al. | 600/203 |
| 8,147,454 B2 | * | 4/2012 | Watanabe et al. | 604/164.04 |
| 8,252,003 B2 | * | 8/2012 | Tanaka et al. | 606/108 |
| 2003/0023259 A1 | | 1/2003 | Dubrul et al. | |
| 2003/0045834 A1 | * | 3/2003 | Wing et al. | 604/161 |
| 2005/0096507 A1 | | 5/2005 | Prosek | |
| 2008/0086080 A1 | | 4/2008 | Mastri et al. | |
| 2009/0182279 A1 | * | 7/2009 | Wenchell et al. | 604/164.04 |
| 2011/0144440 A1 | * | 6/2011 | Cropper et al. | 600/203 |
| 2011/0144447 A1 | * | 6/2011 | Schleitweiler et al. | 600/210 |
| 2011/0144448 A1 | * | 6/2011 | Shelton et al. | 600/216 |
| 2011/0144449 A1 | * | 6/2011 | Ortiz et al. | 600/216 |
| 2011/0144590 A1 | * | 6/2011 | Sakai et al. | 604/167.01 |
| 2011/0319826 A1 | * | 12/2011 | Zisow | 604/164.04 |
| 2012/0022597 A1 | * | 1/2012 | Gephart et al. | 606/279 |

OTHER PUBLICATIONS

Co-pending U.S. Appl. No. 13/217,905, filed on Aug. 25, 2011, Frederick E. Shelton IV.
Co-pending U.S. Appl. No. 13/217,961, filed on Aug. 25, 2011, Frederick E. Shelton IV.
Co-pending U.S. Appl. No. 13/217,973, filed on Aug. 25, 2011, Frederick E. Shelton IV.
Co-pending U.S. Appl. No. 13/217,987, filed on Aug. 25, 2011, Frederick E. Shelton IV.

* cited by examiner

*Primary Examiner* — Laura A Bouchelle
*Assistant Examiner* — Diva K Chander

(57) ABSTRACT

A surgical access device is provided having a cannula and obturator. The cannula has a housing and tube section with an anchor located about the tube section. The obturator has a mechanism to deploy the anchor and adjust the cannula length. The anchor is moveable between a deployed and undeployed state where the undeployed state facilitates insertion and removal of the access device and the deployed state assists in fixation of the cannula in an anatomic structure. Anchor deployment is independent of cannula length adjustment.

17 Claims, 23 Drawing Sheets

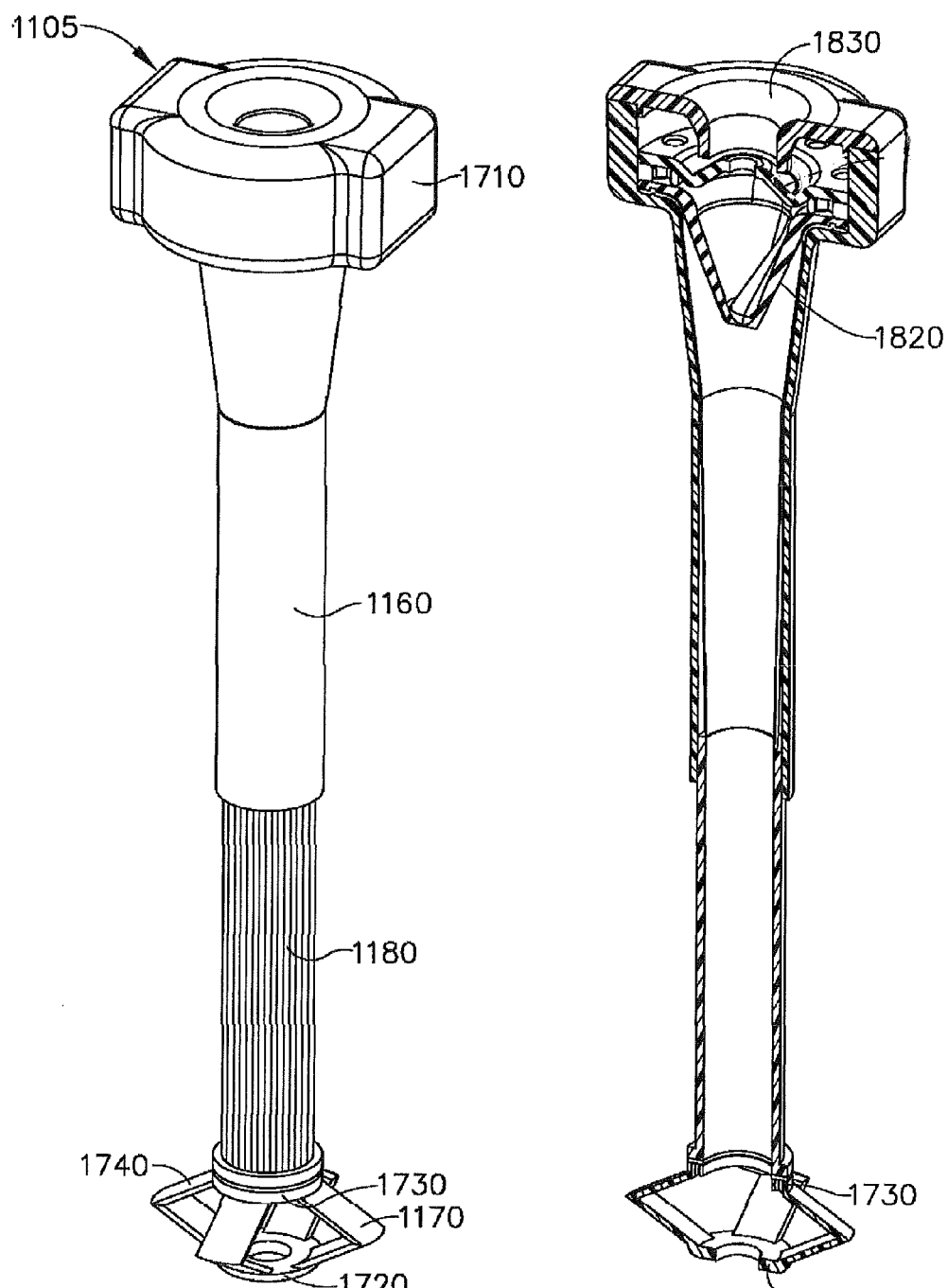

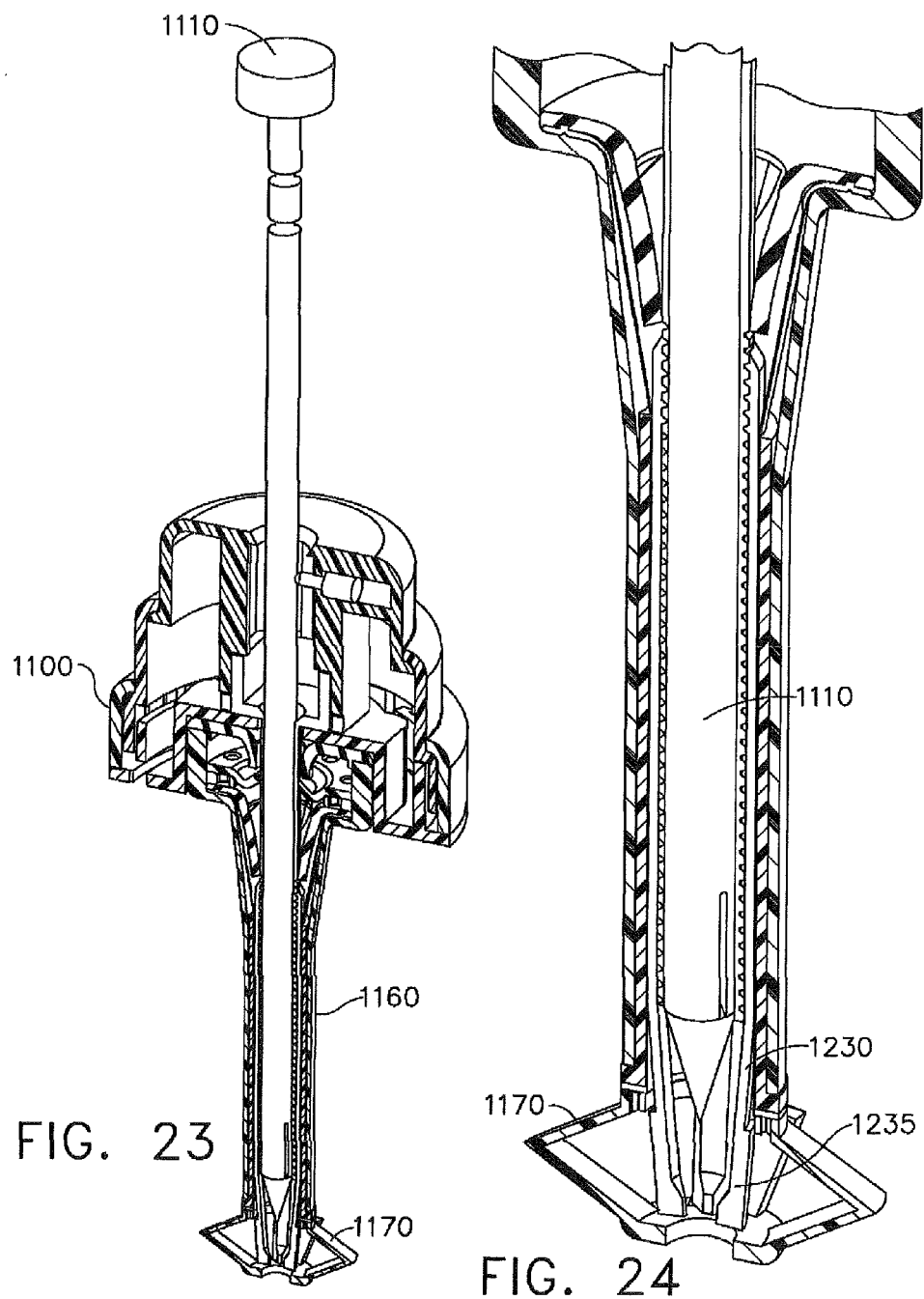

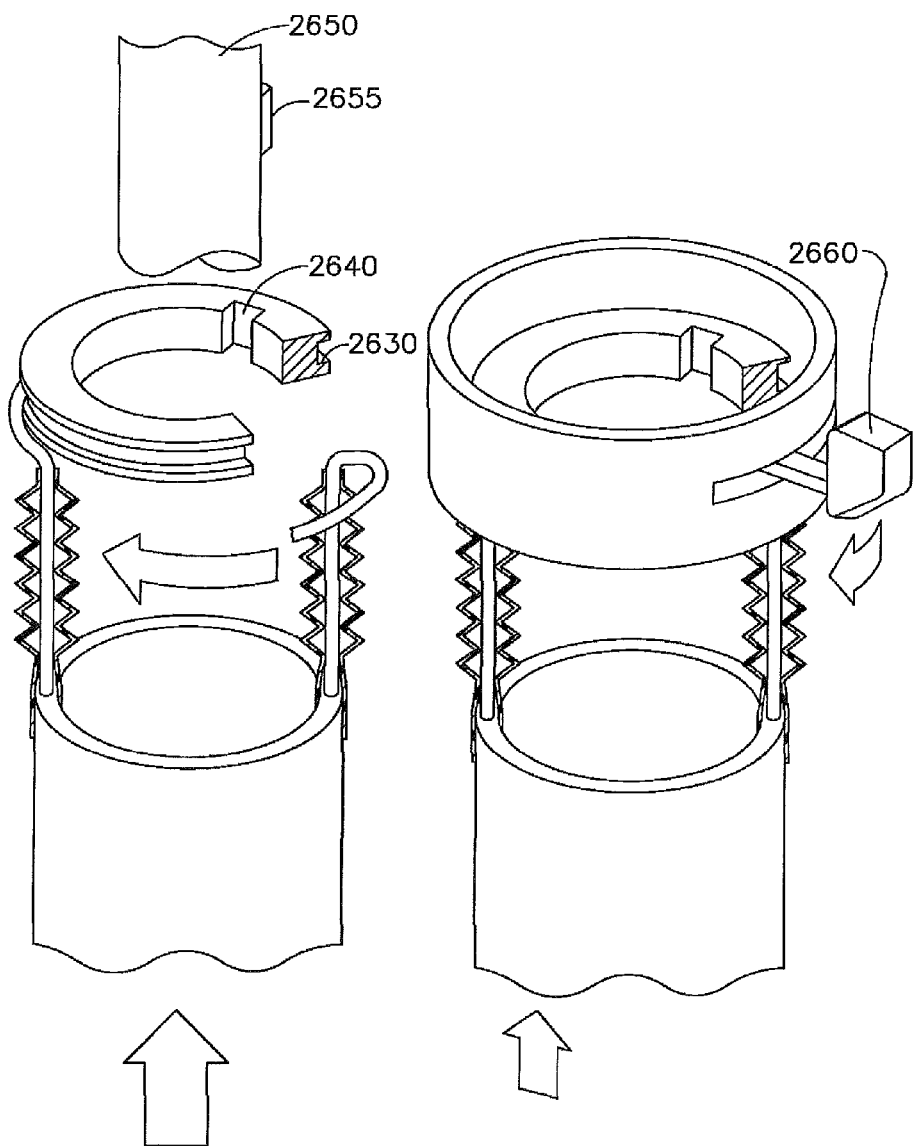

SURGICAL ACCESS DEVICE WITH ADJUSTABLE CANNULA

BACKGROUND

The present invention relates in general to surgical devices and procedures, and more particularly to minimally invasive surgery.

Surgical procedures are often used to treat and cure a wide range of diseases, conditions, and injuries. Surgery often requires access to internal tissue through open surgical procedures or endoscopic surgical procedures. The term "endoscopic" refers to all types of minimally invasive surgical procedures including laparoscopic, arthroscopic, natural orifice intraluminal, and natural orifice transluminal procedures. Endoscopic surgery has numerous advantages compared to traditional open surgical procedures, including reduced trauma, faster recovery, reduced risk of infection, and reduced scarring. Endoscopic surgery is often performed with an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. Surgical access devices are often used to facilitate surgical manipulation of internal tissue while maintaining pneumoperitoneum. For example, trocars are often used to provide a port through which endoscopic surgical instruments are passed. Trocars generally have an instrument seal, which prevents the insufflatory fluid from escaping while an instrument is positioned in the trocar. Endoscopic surgery may also be performed in the absence of insufflatory gas. For example, minimally invasive thoracic surgery may be performed in the absence of insufflatory gas.

While surgical access devices are known, no one has previously made or used the surgical devices and methods in accordance with the present invention.

BRIEF DESCRIPTION OF DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, the figures are not necessarily drawn to scale, but rather to illustrate the principles of the invention.

FIG. 17 is another expression of a surgical trocar access device depicting a surgical trocar cannula having a lower cannula with a ribbed surface and further having cannula anchors in a fully deployed state;

FIG. 18 is a partial cross-sectional view of the FIG. 17 cannula;

FIG. 23 is a partial cross sectional view of the FIG. 21 surgical access device with the anchor deployed and the cannula length reduced to its shortest length;

FIG. 24 is a close up of the distal end of the FIG. 23 surgical access device with the obturator shaft partially removed;

FIG. 25 depicts another expression of a trocar cannula length adjusting device;

FIGS. 26, 26A and 26B depict an exploded view of the FIG. 25 cannula housing assembly for performing cannula length adjustment.

DETAILED DESCRIPTION

Figure 1:
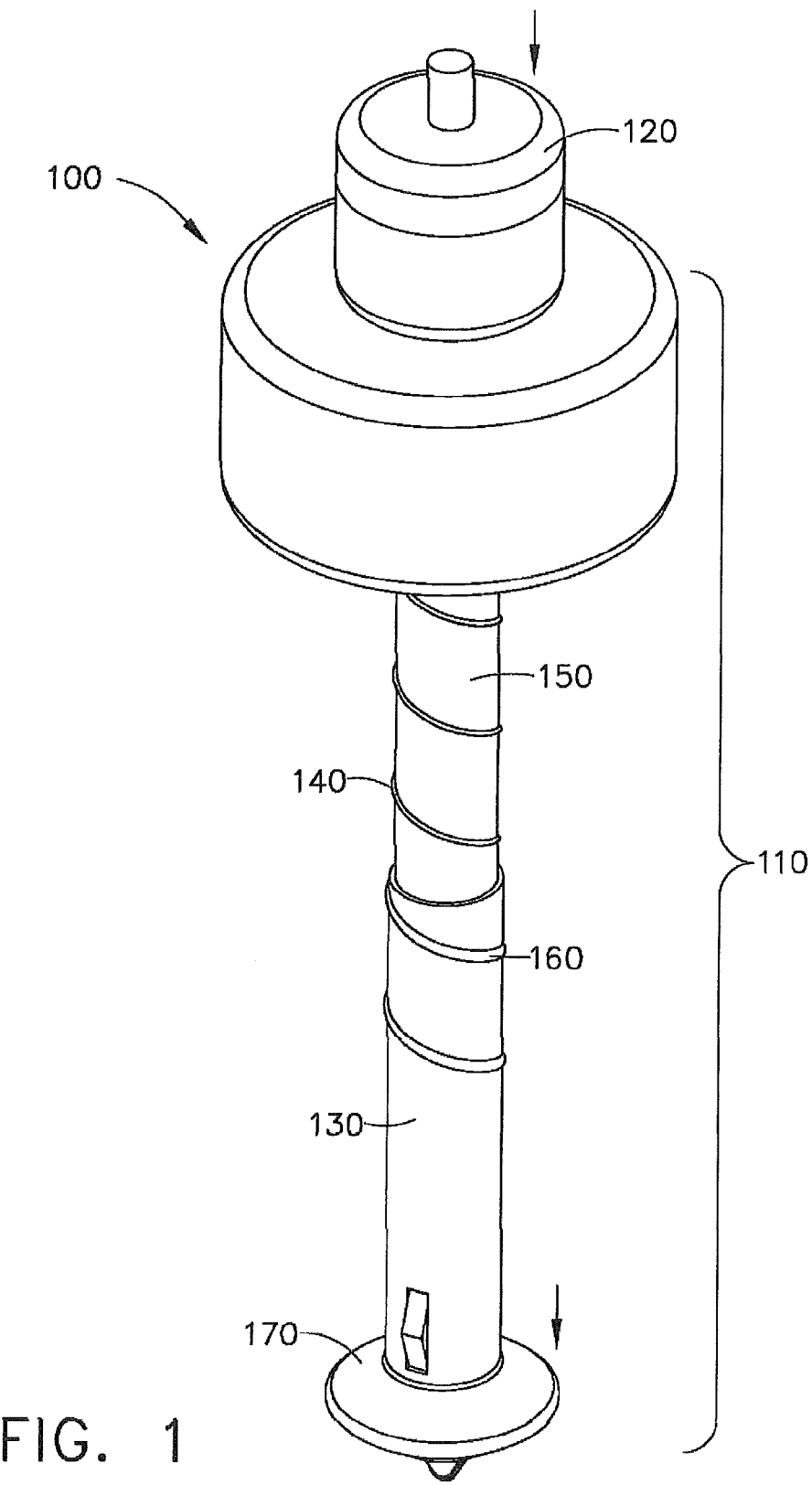
FIG. 1 depicts is an isometric view of a surgical trocar having a cannula and obturator with a cannula anchor in a deployed state.
Figure 2:
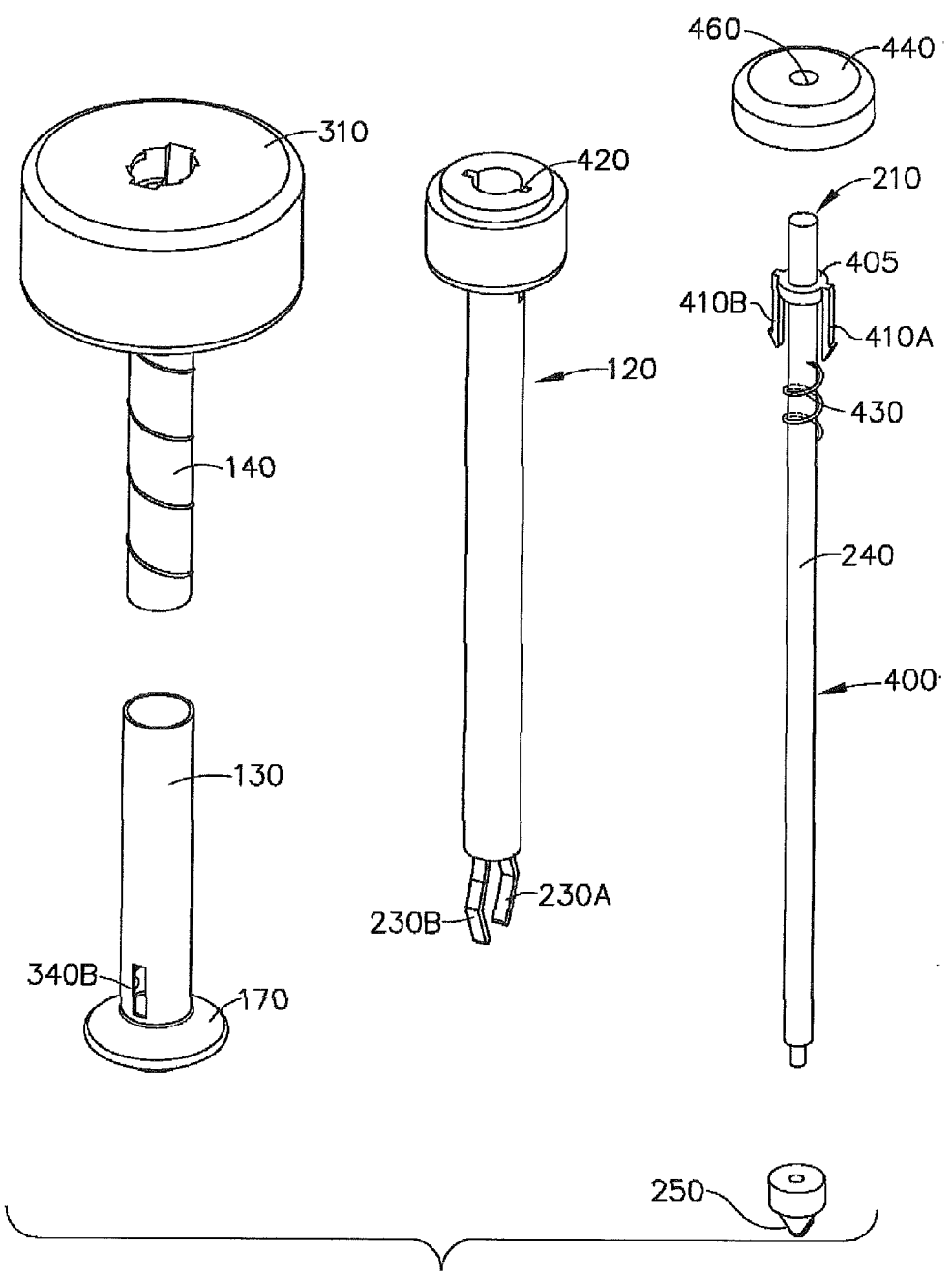
FIG. 2 is an exploded view of the surgical trocar of FIG. 1.

The devices and methods disclosed herein relate to providing access to an operative site and in particular to surgical trocar access devices that provide access to the abdomen and thoracic cavity. The trocars permit insertion and removal of surgical instruments during an operative procedure and are particularly suited for minimally invasive surgical procedures. Expressions of a surgical trocar will be described in detail with reference to drawings wherein like reference numerals designate identical or corresponding elements in each of the several views.

For purpose of explanation and illustration and not limitation, an isometric view of one expression of a surgical trocar access device, or trocar, is shown in FIG. 1 and is designated by reference number 100. Other expressions of surgical trocars are presented in FIGS. 2-27, as will be described fully herein.

Referring to FIG. 1, trocar 100 is comprised of a cannula 110 and an obturator 120 inserted in cannula 110. In one expression of the trocar 100, the cannula is comprised of two cannula tubes, 130 and 140. Distal cannula tube 130 is adapted to receive proximal cannula tube 140. In one expression of the trocar 100, distal cannula tube 130 may be flexible and include impressed threads 160. Proximal cannula tube 140, in one expression, is generally rigid in its construction and may further include threads 150 which may be adapted to mate with impressed threads 160. Trocar 100 also includes a distal anchor 170 which assists in anchoring cannula 110 in an abdominal wall or any other suitable anatomy.

Figure 3:
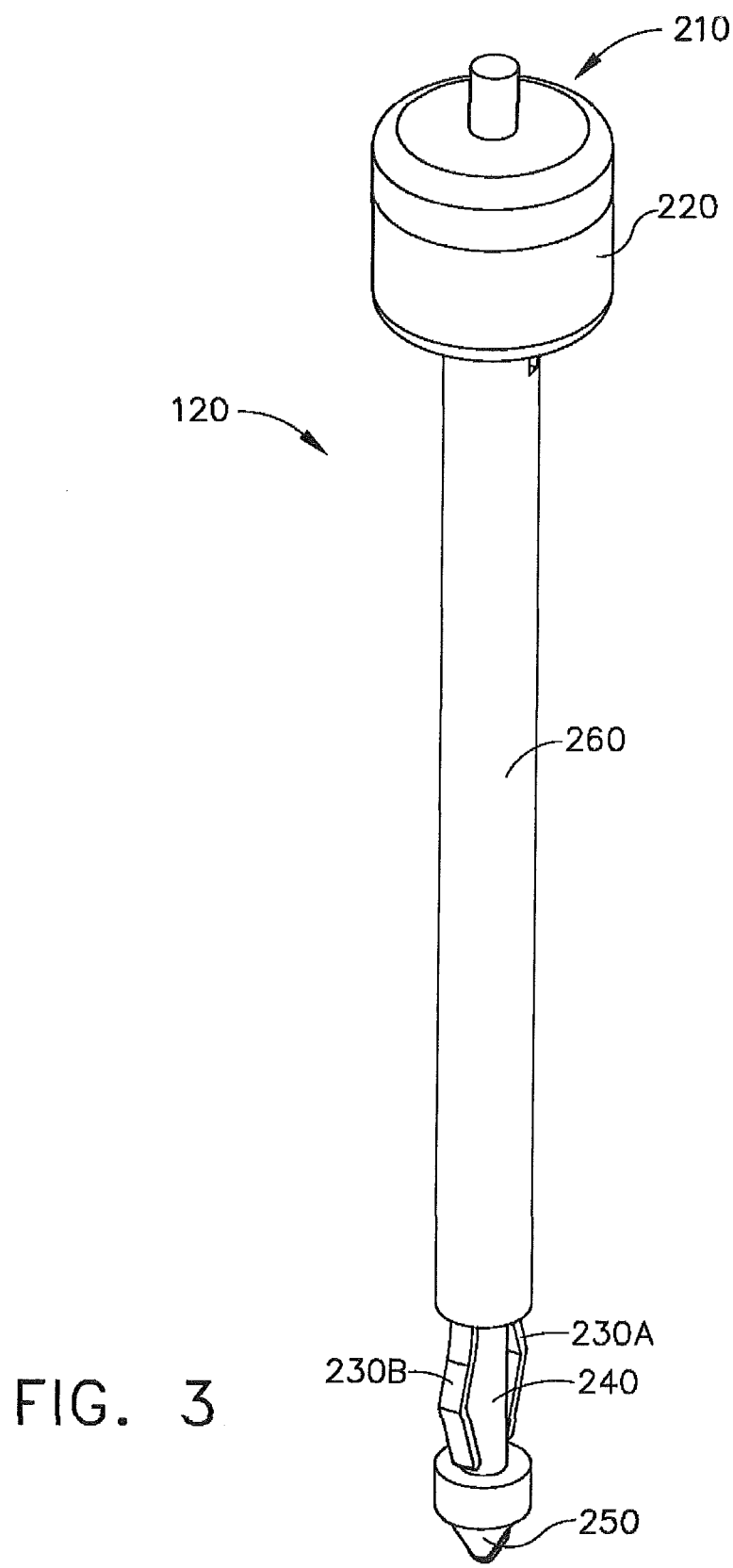
FIG. 3 is an isometric view of the FIG. 1 trocar obturator.

Referring now to FIG. 3, trocar obturator 120 is provided to facilitate insertion of cannula 110 into an appropriate anatomic structure. Obturator 120 is provided with an anchor deployment button 210. Obturator 120 includes finger grip area 220 to facilitate insertion and removal of obturator 120 from cannula 110. Obturator 120 further includes obturator tube 260 and may further include distal anti-rotation locks 230A and 230B and anchor deployment shaft 240. Anti-rotation locks 230A and 230B, extend distally from a distal end of obturator 120 in a cantilevered manner and may be disposed about the medial surface of tube 260. In one expression, locks 230A and 230B have a triangular shape terminating in a peak. Locks 230A and 230B are in mechanical communication with openings 340A and 340B in distal cannula tube 130, and may be spring-biased to facilitate insertion into cannula 110. Obturator 120 may further include a tip 250 to facilitate insertion of the trocar 100 into an anatomic structure. Tip 250 may comprise a flat blade, pyramidal blade, an optical dilation tip, blunt tip or the like. Obturator 120 may be adapted to accommodate an endoscopic camera system, as in known in the art.

Figure 4:
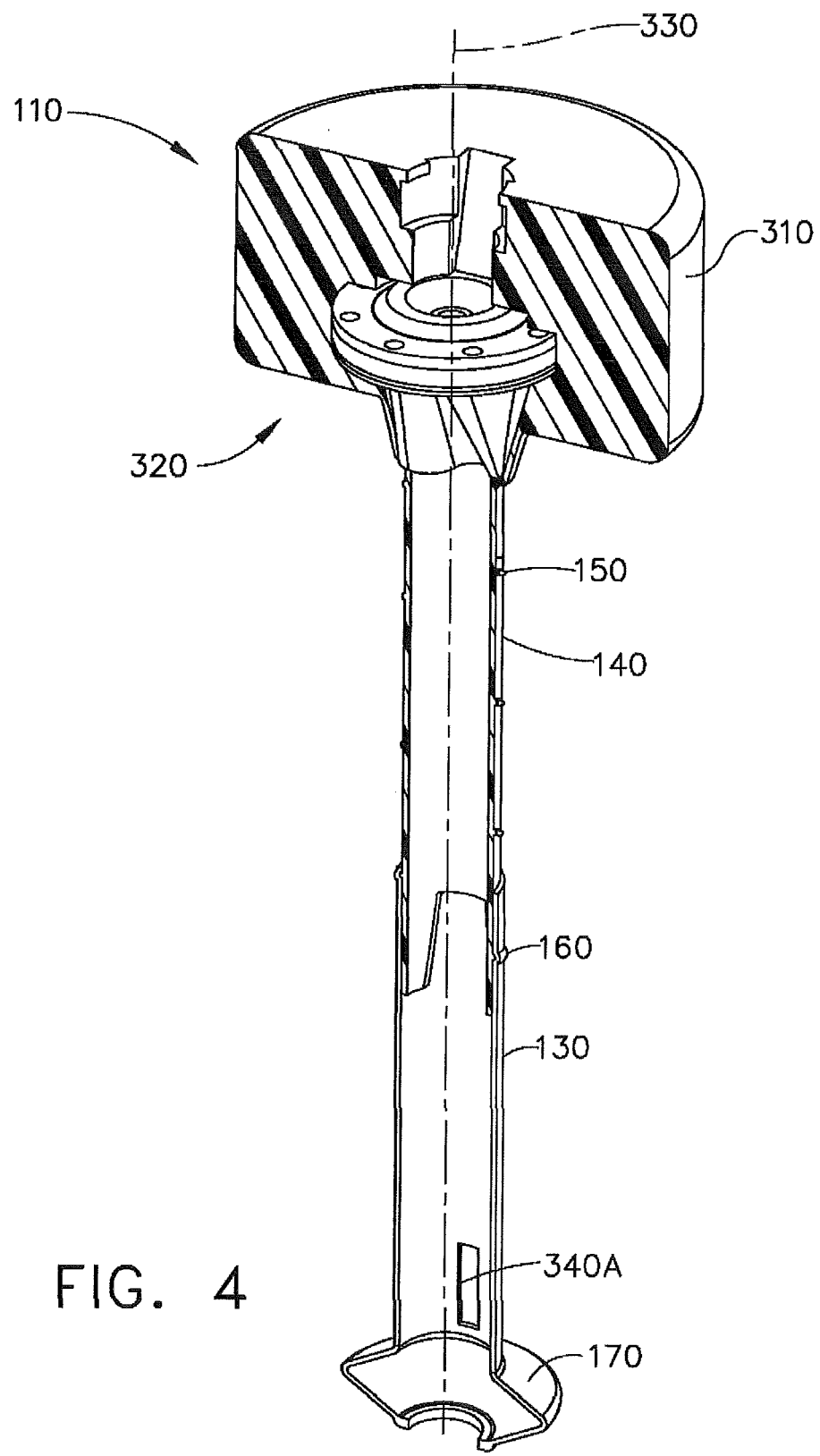
FIG. 4 is a partial cross-sectional view of a surgical trocar having a cannula anchor in a deployed state.

Cannula 110 is provided with a seal 320 which may be located in cannula housing 310, as seen in FIG. 4. Seal 320 may be comprised of a duckbill valve and an elastomeric annular seal as shown in FIG. 4. Seal 320 may be provided with a flapper valve in place of the duckbill or may be provided with only an elastomeric annular seal, or any combination thereof, as is known in the art or any other seal to prevent the escape of insufflations gas. Seal 320 may be sized to accommodate various diameter surgical instruments e.g. 3 mm to 12 mm.

Cannula housing 310 is generally cylindrical and sized to provide a gripping surface for insertion of trocar 100 into an anatomic structure. Housing 310 is also sized to contact the exterior surface of an anatomic structure and is larger than an incision through which the cannula tube 130, 140 is passed. Housing 310, in the present expression, is cylindrical in nature but may be any shape or size such that it can be gripped and will not pass into an incision. Cannula housing 310 and cannula tubes 130, 140 are hollow in nature and define a lumen 330. Lumen 330 is sized to permit the passage of surgical instruments and may accommodate surgical instruments of different diameters e.g. 3 mm to 12 mm. Extending distally from cannula housing 310, cannula tube 140 contains threads 150 which are designed to mate with impressed threads 160 on distal cannula tube 140. Cannula tube 140 is further provided with openings 340A and 340B (not pictured) to mate with distal anti-rotation locks 230A and 230B.

Distal cannula 130 further comprises cannula anchor 170, located adjacent the distal end of cannula tube 130, but may be located anywhere along cannula tube 130. Anchor 170 is, in one expression, formed of pliable elastomer and may be deformed longitudinally.

Referring now to FIG. 4, an exploded view of trocar 100 is provided. Anchor deployment assembly 400 of obturator 120 is arranged with anchor locks 410A and 410B disposed about anchor shaft 240. Anchor spring 430 is further disposed about anchor shaft 240 and may move freely between locks 410A and 410B and tip 250. Anchor deployment button 210 defines the proximal end of anchor deployment shaft 240. Tip 250 defines the distal end of shaft 240 and may be removably attached to shaft 240 to permit attachment of different trocar tips. Anchor locks 410A and 410B, in one expression, extend distally from ring 405 in a proximal-to-distal cantilevered manner along shaft 240 defining a gap such that the anchors are medially resiliently deflectable and may further have chamfered distal surfaces to facilitate insertion into obturator 120 and cannula housing 310. Anchor lock slots 420 are dimensioned to accommodate anchor locks 410A and 410B and permit rotational force transfer from housing 220 to anchor locks 410A and 410B. Anchor deployment assembly further comprises an anchor shaft cap 440 that defines a medial annulus 460 dimensioned to mate with button 210 such that button 210 protrudes from a proximal side of cap 440.

Figure 5:
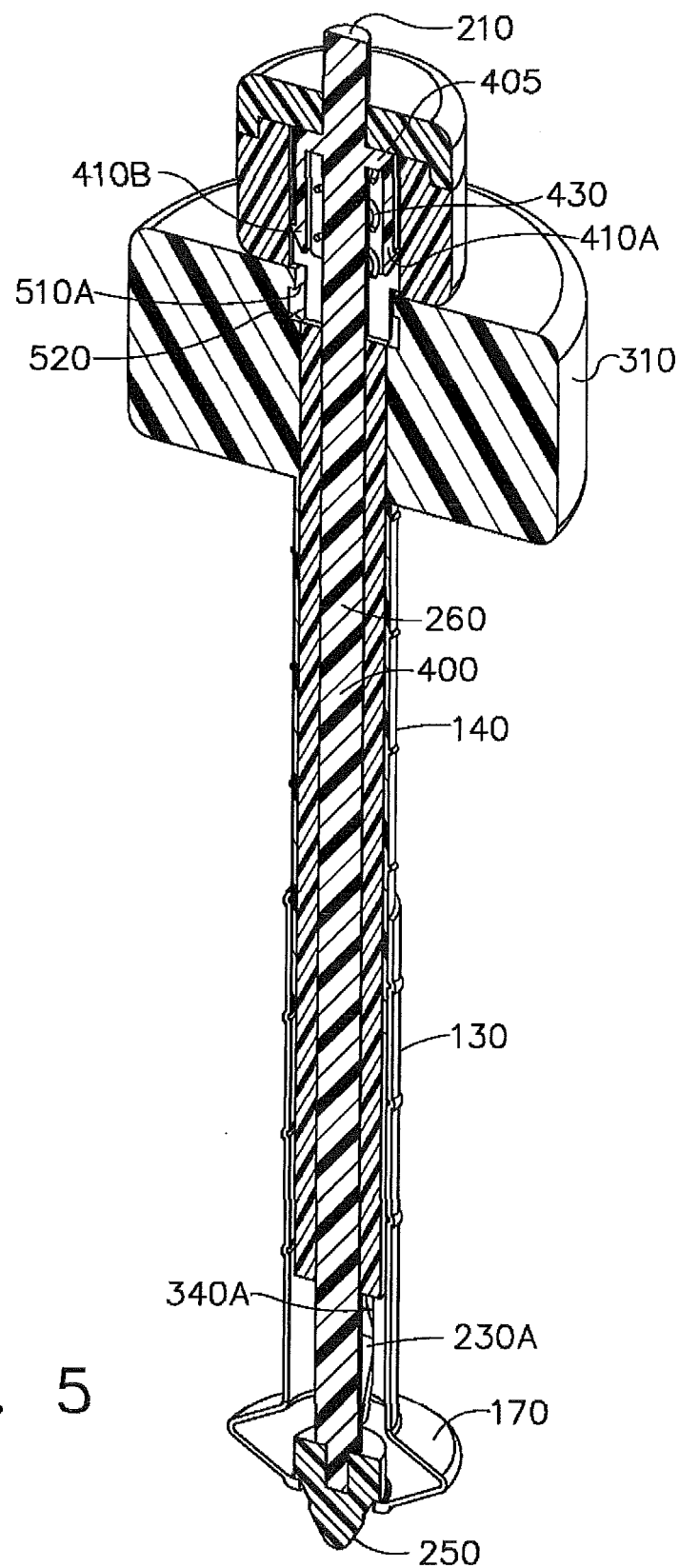
FIG. 5 is a partial cross-sectional view of a surgical trocar with a cannula anchor in a deployed state and an obturator in an unarmed state.

FIG. 5 is a partial cross sectional view of trocar 100 in an unarmed state. Anchor deployment assembly 400 is inserted through obturator 120 and obturator 120 is inserted into cannula 110 forming trocar 100. Angled surface of anchor locks 230 creates medial deflection of locks 230 upon insertion into cannula 110. When locks engage openings 340, peak of locks 230 protrudes into opening permitting the transfer of rotational force from the obturator 120 to cannula tube 130 creating a spline-groove type engagement.

A flange portion of tip 250 may engage anchor 170 when obturator 120 is inserted, permitting tip 250 to extend a predetermined distance beyond anchor 170. As shown, tip 250 engages anchor 170 as obturator housing 220 abuts cannula housing 310. Cannula housing 310 is provided with at least two anchor deployment detents 510A and 510B to receive and hold locks 410A and 410B. Detents 510A and 510B may be disposed in an annular fashion along the medial surface of cannula housing 310 and, in one expression, span less than 90° each. In an unarmed state, anchor locks 410A and 410B are disposed above detents 510A and 510B such that obturator 120 is axially slideable with respect to cannula 110. Spring 430 may be axially slideable along anchor tube 240 between ring 405 and cannula flange 520 when trocar 100 is unarmed. Locks 230A and 230B engage cannula openings 340A and 340B and slide axially within openings 340A and 340B, permitting obturator 120 to move axially while locks 230 are engaged with openings 340.

Figure 6:
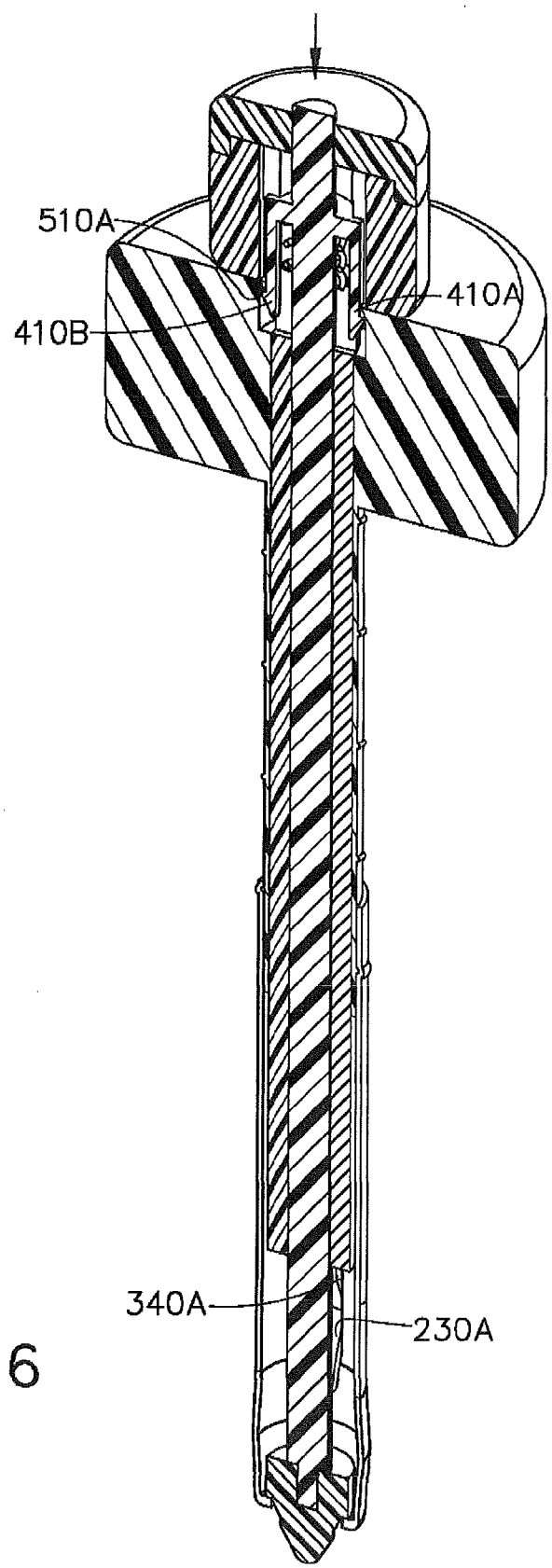
FIG. 6 is a partial cross-sectional view of a surgical trocar with a cannula anchor in an undeployed state and an obturator in an armed state.

When anchor deployment button 210 is depressed, anchor deployment shaft 400 moves in a distal longitudinal direction relative to obturator 120 and cannula 110. As button 210 is depressed, lateral flange of tip 250 engages medial flange of anchor 170 thereby transferring force from button 210 axially to anchor 170. Anchor 170 extends distally and collapses into the approximate diameter of cannula tube 130 as shown in FIG. 6. In one expression of trocar 100, when anchor 170 is elongated such that its diameter is appropriate for insertion through an incision, chamfered surfaces of anchor locks 410A and 410B medially deflect locks 410A and 410B against detents 510A and 510B until 410A and 410B are seated below detents 510A and 510B creating an interference fit and preventing distal axial motion of obturator 120 relative to cannula 110. Openings 340A and 340B are dimensioned such that rotation locks 230A and 230B remain engaged with openings 340A and 340B as obturator 120 is moved in a distal axial direction from an unarmed to an armed state. In an armed state, spring 430 is compressed between ring 405 and detents 510A and 510B, creating a proximal axial force on anchor deployment assembly 400 relative to obturator 120.

Figure 7:
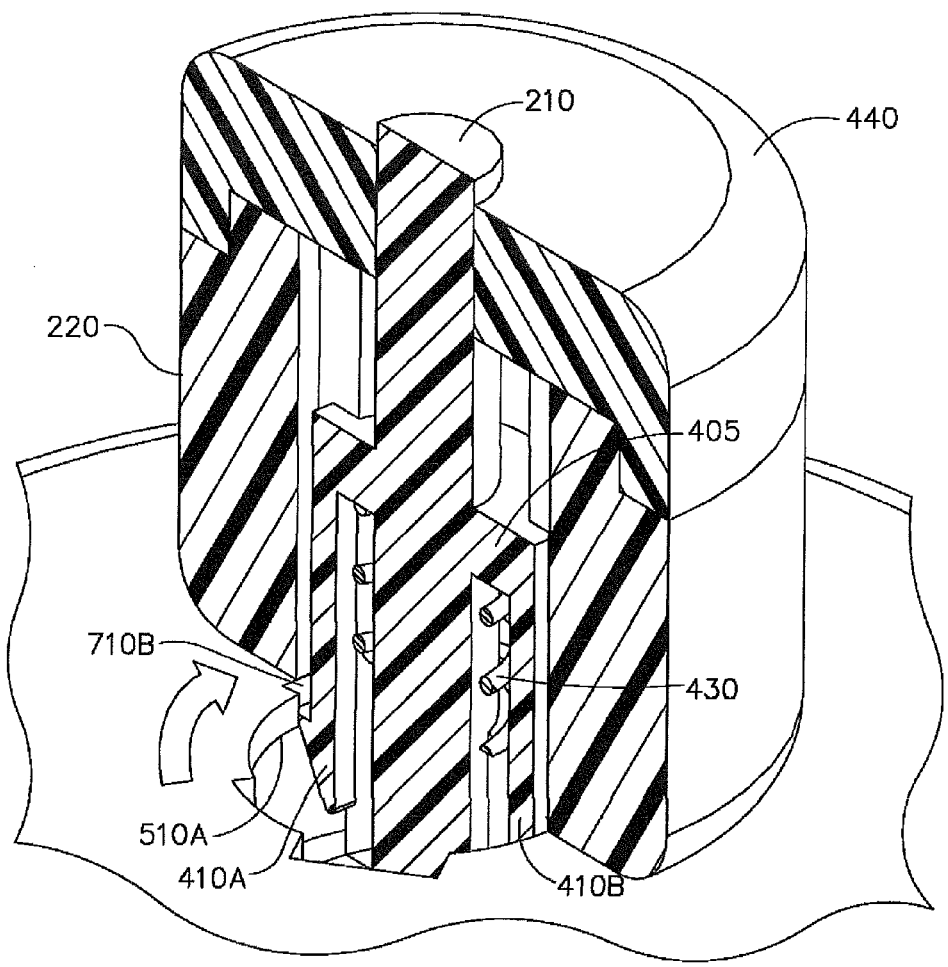
FIG. 7 is a partial cross-sectional view of a surgical trocar cannula housing with an obturator inserted into the housing, further depicting rotation of the obturator to release the cannula anchor.
Figure 8:
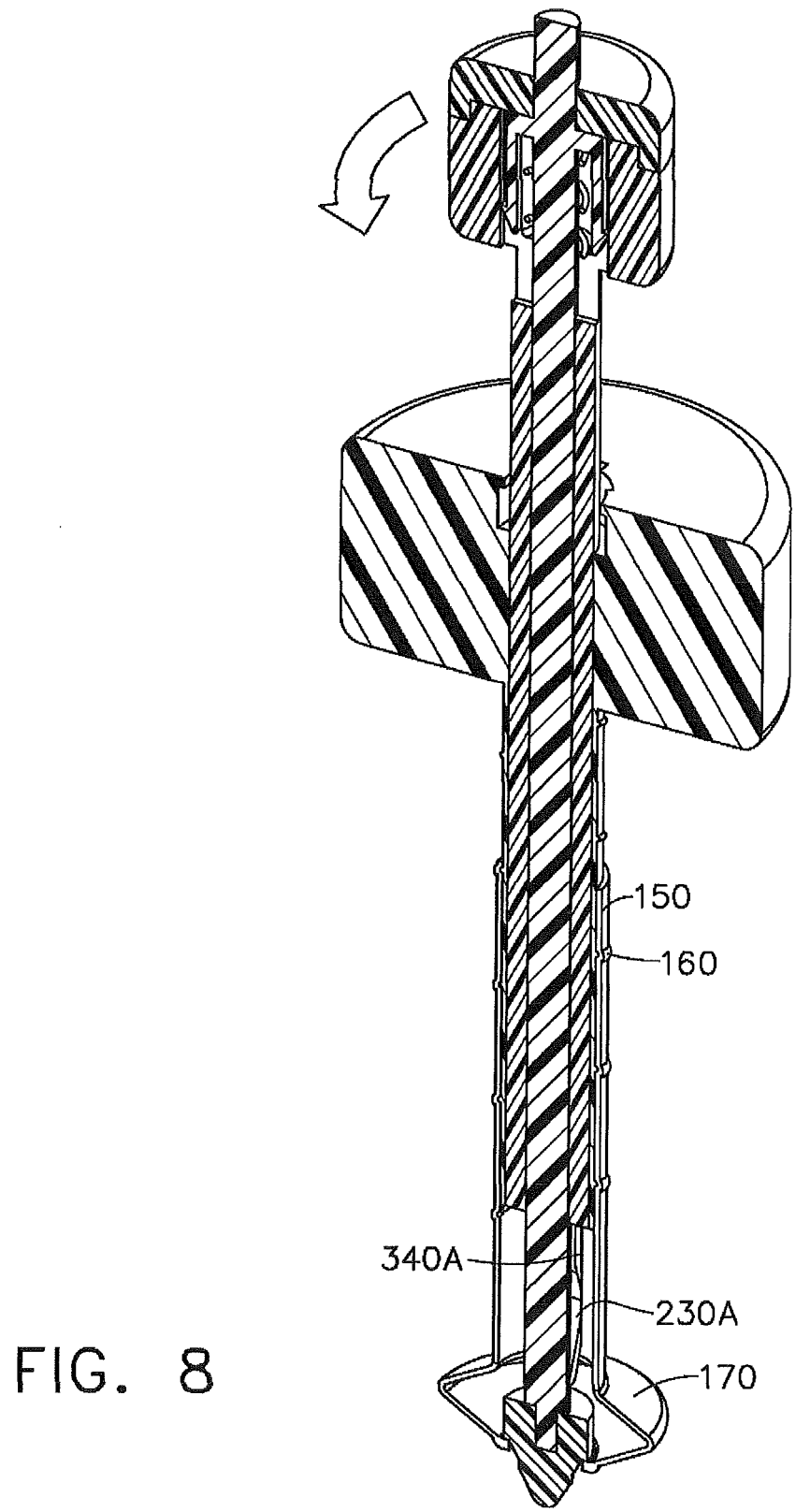
FIG. 8 is a partial cross sectional view of a cannula in a shortened state where the cannula anchor has deployed.

FIG. 7 is a partial cross sectional view of the proximal portion of trocar 100 in an armed state. As described previously, anchor locks 410A and 410B seat below detents 510A and 510B preventing distal axial motion of obturator 120 relative to cannula 110. As depicted in FIG. 7, cannula housing 310 is provided with detents 510 and detent openings 710A and 710B. After trocar 100 is inserted through an incision into an anatomic structure in an armed state, it is necessary to deploy anchor 170 to provide fixation in the anatomic structure.

By rotating obturator housing 120, anchor locks 410A and 410B align with detent openings 710A and 710B; force from spring 430 exerts proximal axial force on ring 405 and moves anchor deployment shaft 400 in a proximal direction away from anchor 170, relieving tension on anchor 170 allowing anchor 170 to resume a deployed shape as depicted in FIG. 1. Button 210 returns to an unarmed position as depicted in FIG. 5 and trocar 100 is once again in a unarmed state. In this state, should obturator tip 250 be pressed axially against an anatomical structure, there is no concomitant force to counteract the movement of anchor 400 from moving in a manner away from the anatomic structure.

Figure 9:
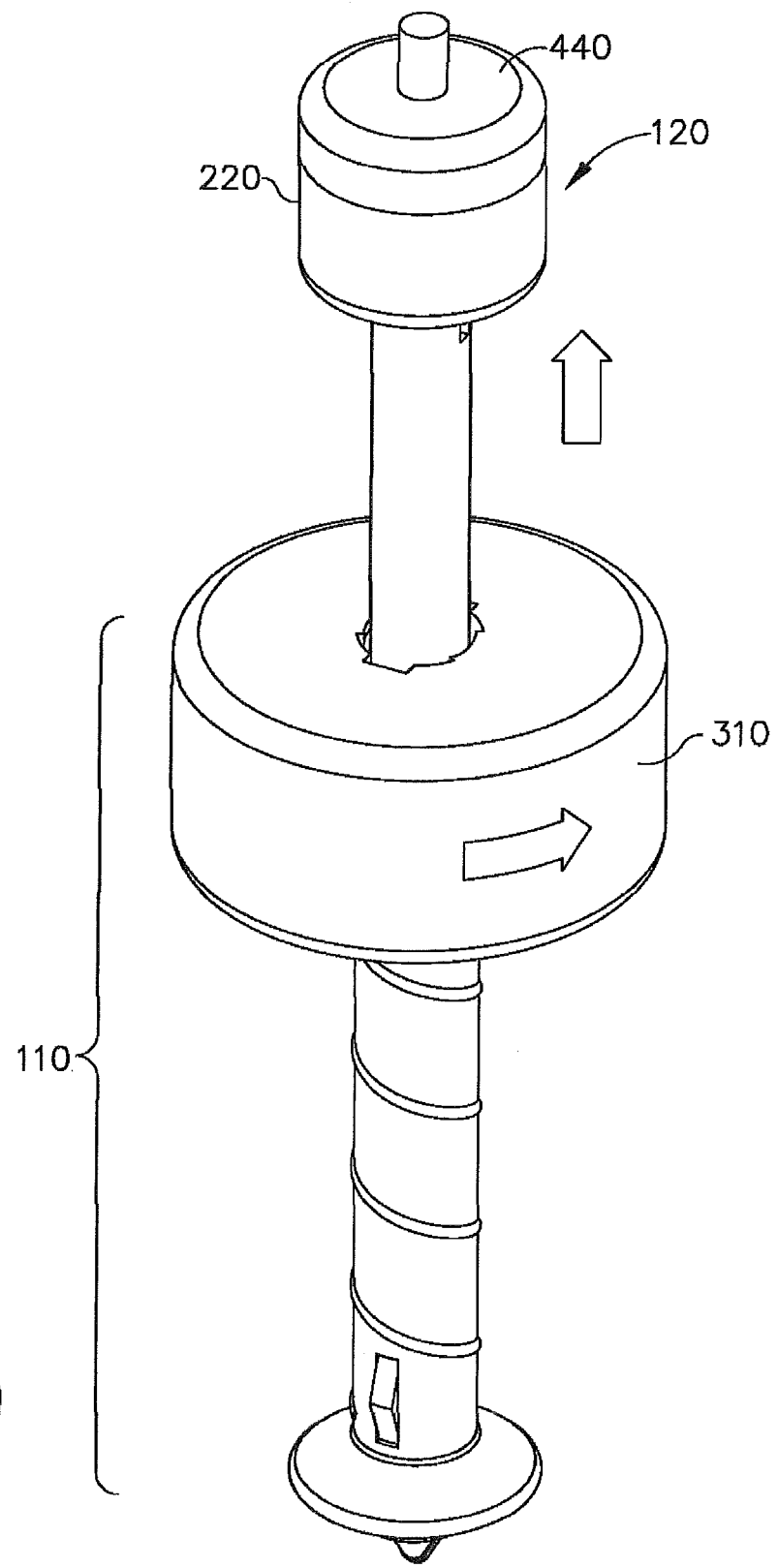
FIG. 9 depicts rotation of the cannula housing to change the length of the surgical trocar cannula.
Figure 10:
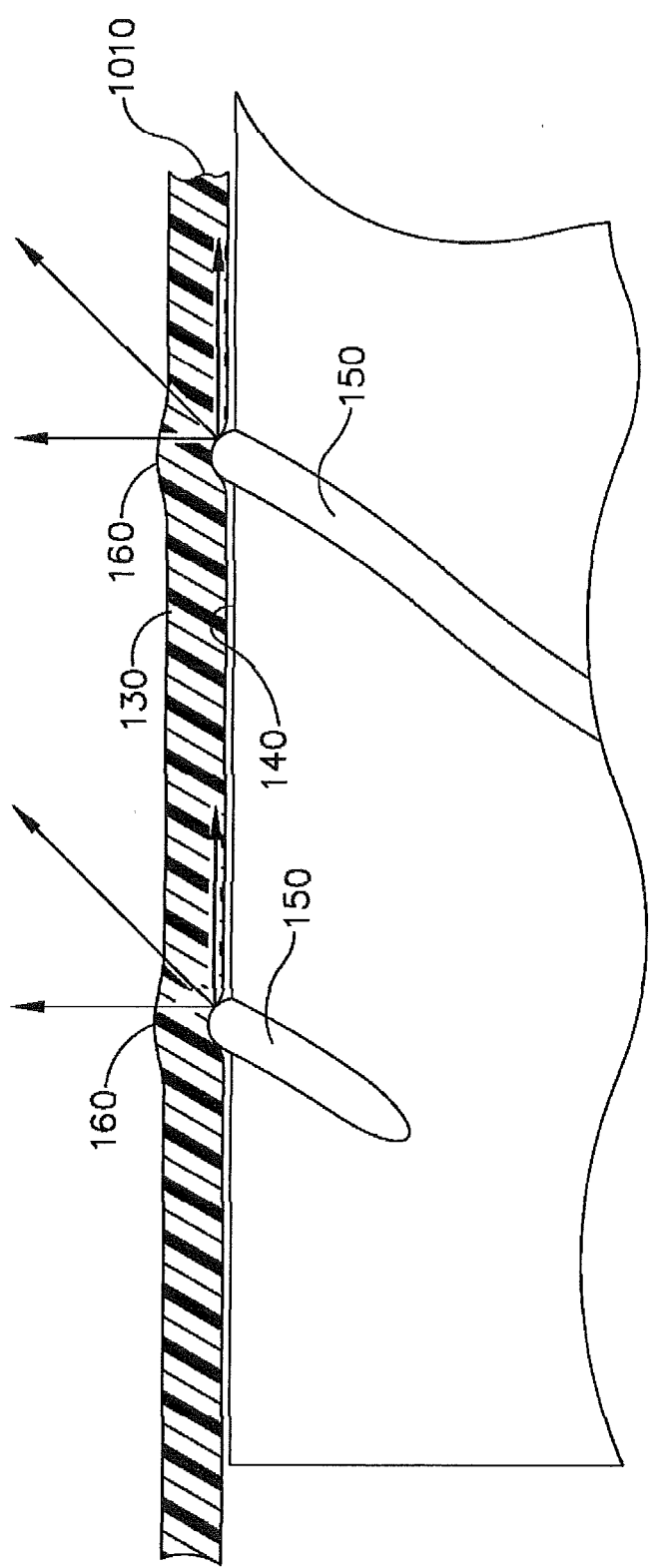
FIG. 10 depicts threads or raised surfaces of the exterior cannula tube housing contacting operative site tissue.

Once trocar 100 is inserted into an anatomic structure and disarmed, it may be desirable to shorten the length of cannula 100. By rotating obturator housing 220 in a counterclockwise manner (depending upon the orientation of threads 150 and 160) while holding cannula housing 310 stationary, rotational force is transferred from housing 220 through locks 230A and 230B to distal cannula openings 340A and 340B thereby rotating distal cannula 130 in a counterclockwise manner. Obturator 220 may be held stationary while housing 310 is rotated, as shown in FIG. 9. Threads 160 engage proximal cannula threads 150 and drive distal cannula 130 proximally over proximal cannula 140, thereby shortening the in vivo length of cannula 110. Once a desired in vivo length is achieved, obturator 120 is removed from cannula 110 permitting insertion and removal of surgical instruments. Anchor 170 provides axial resistance to removal of cannula 110 by contacting the inner surface of an anatomic structure when proximal axial force is applied to cannula 110. Threads 150 and 160 contact the anatomic structure wall 1010 (e.g. abdominal wall) as shown in FIG. 10, further providing resistance to proximal and distal motion of cannula 110 as instruments are inserted and removed from cannula 110.

Figure 11:
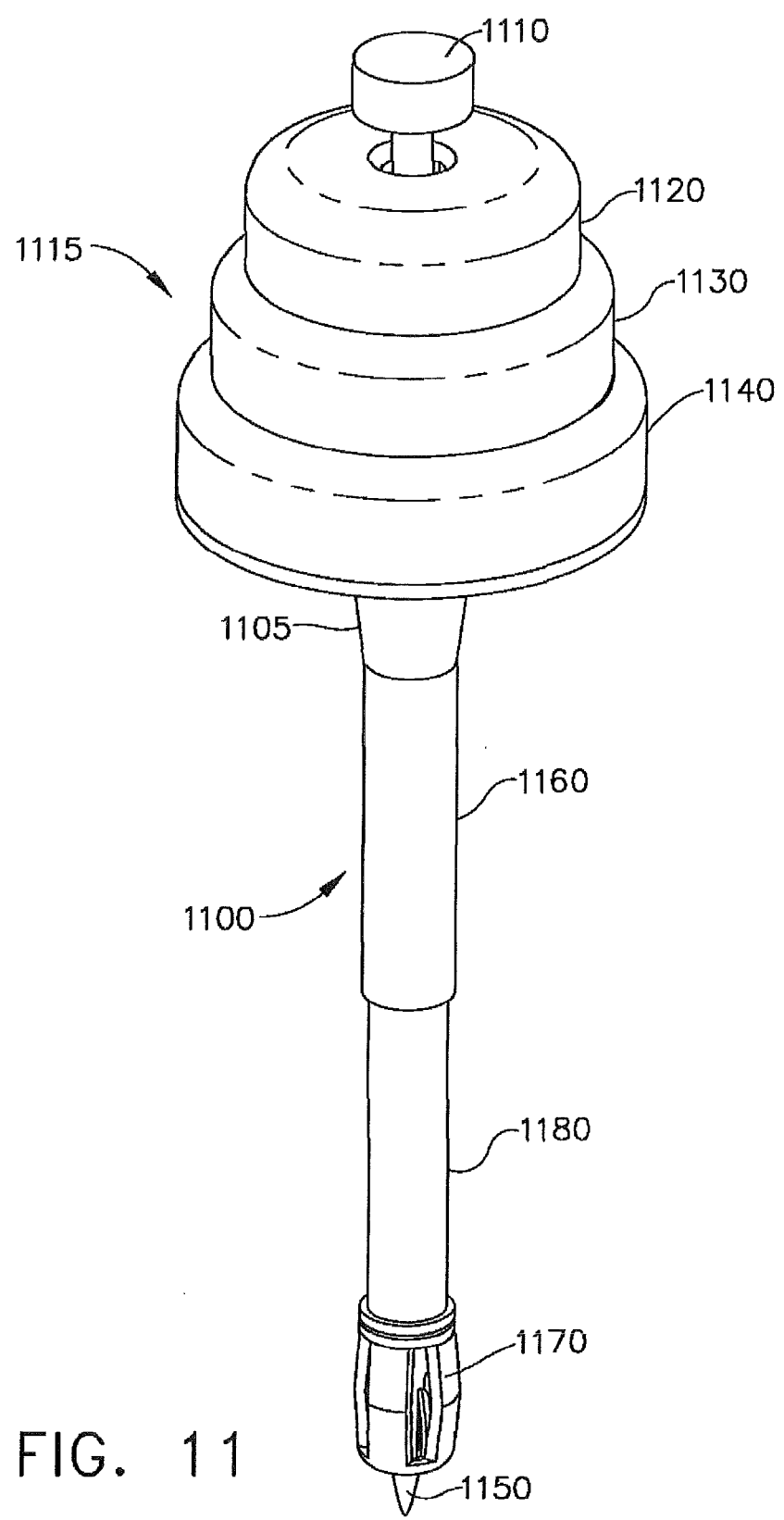
FIG. 11 is an isometric view of another expression of the surgical trocar access device depicting the cannula anchor in an undeployed state and the obturator in an armed state.

Referring now to FIG. 11, another expression of a surgical trocar 1100 is depicted. As shown, anchor 1170 is under tension in a collapsed state. In this position, obturator shaft 1110 is fully extended through cannula 1105 and trocar 1100 is in an armed state, ready for insertion through an incision into an anatomic structure. Cannula 1105 is comprised of two cannula tubes, proximal tube 1160 and distal tube 1180 to which anchor 1170 is attached. Anchor 1170 may be formed from tube 1180 thereby creating a contiguous tube-anchor structure. Obturator housing 1115, in one expression, is formed from three interleaved cylindrical housings 1120, 1130 and 1140, which are more fully depicted in FIG. 12.

Figure 12:
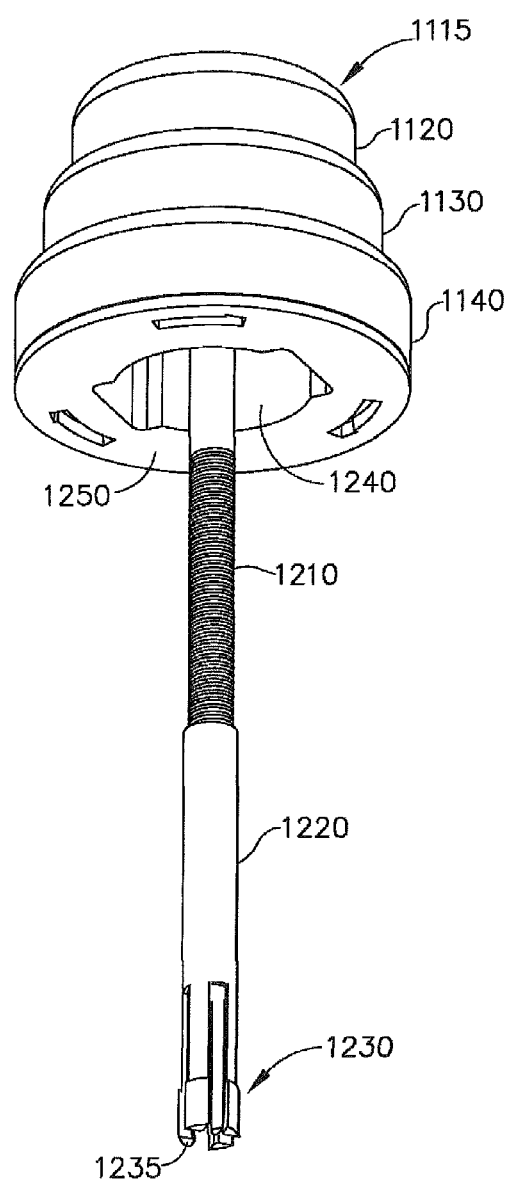
FIG. 12 is an isometric view of a surgical trocar access device obturator having a two-piece tube with a threaded length adjustment feature.

FIG. 12 illustrates obturator housing 1115 with proximal obturator tube 1210 attached thereto. In one expression of the instant surgical access device, tube 1210 is provided with a threaded surface designed to mate with a threaded interior on distal obturator tube 1220 (see FIG. 13 tube 1220). When housing 1115 is rotated, tube 1210 is concomitantly rotated driving tube 1210 into distal tube 1220 when tube 1220 is held stationary relative to tube's 1210 rotation. Tube 1220 is provided with locking fingers 1230 at its distal end to engage obturator shaft 1110 when inserted into obturator housing 1115. Radial locks 1235 are formed on a lateral surface of fingers 1230 to engage anchor 1170 and distal cannula tube 1180. Obturator housing 1115 is provided with a base 1250 to receive housing 1140. Base 1250 defines a medial opening 1240 which may be adapted to receive cannula 1105 housing therein.

Figure 13:
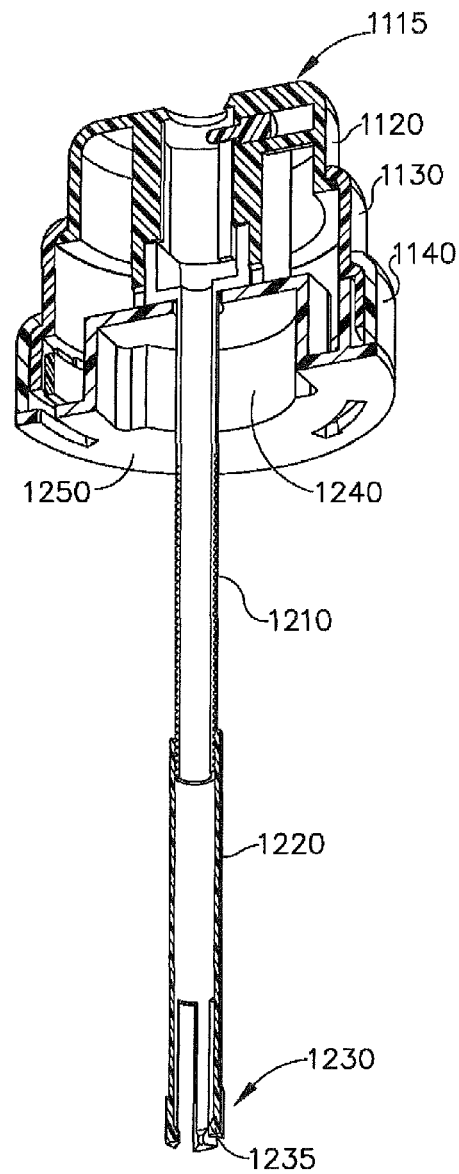
FIG. 13 is a partial cross sectional view of the FIG. 12 trocar.

Partial cross sectional view of obturator housing 1115 in FIG. 13 depicts the interleaved nature of cylindrical housings 1120, 1130 and 1140. Cylindrical housings 1120, 1130, 1140 engage and may press fit onto obturator housing base 1250 to form a contiguous surface. Proximal axial force exerted on proximal-most housing 1120 in turn exerts axial force on housing 1130 which, in turn, exerts axial force on housing 1140 facilitating removal of obturator 1115 from cannula. Housing 1115 further contains obturator shaft detent pin 1310 which engages detents on obturator shaft 1110.

Figure 14:
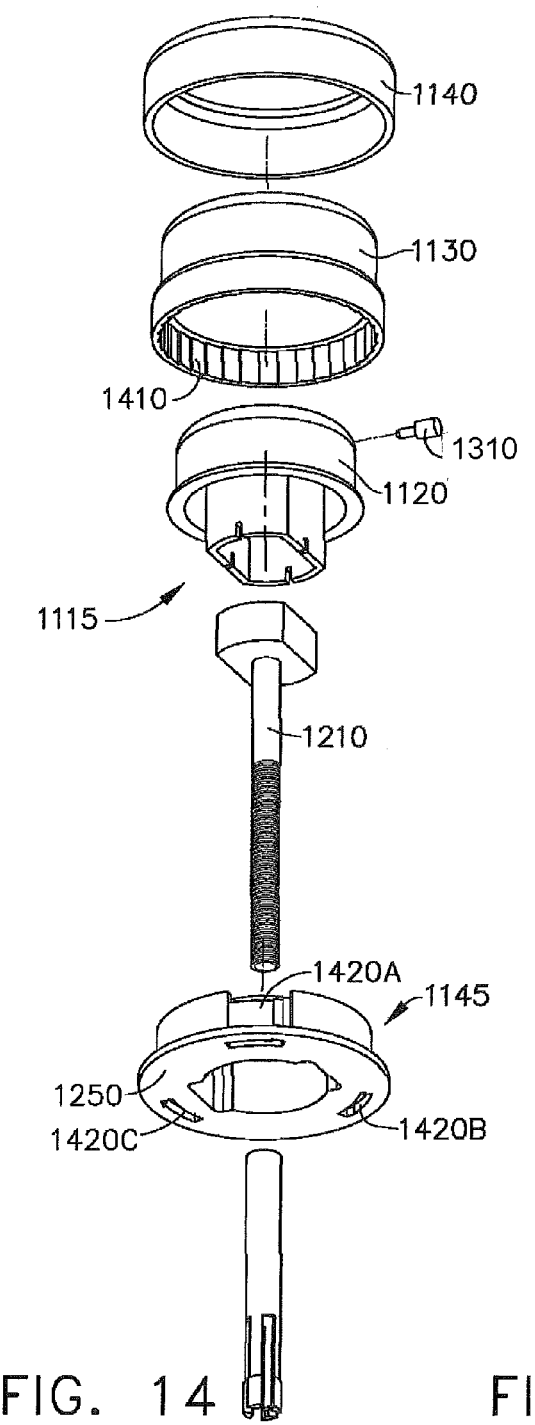
FIG. 14 is an exploded view of FIG. 13 obturator components.
Figure 15:
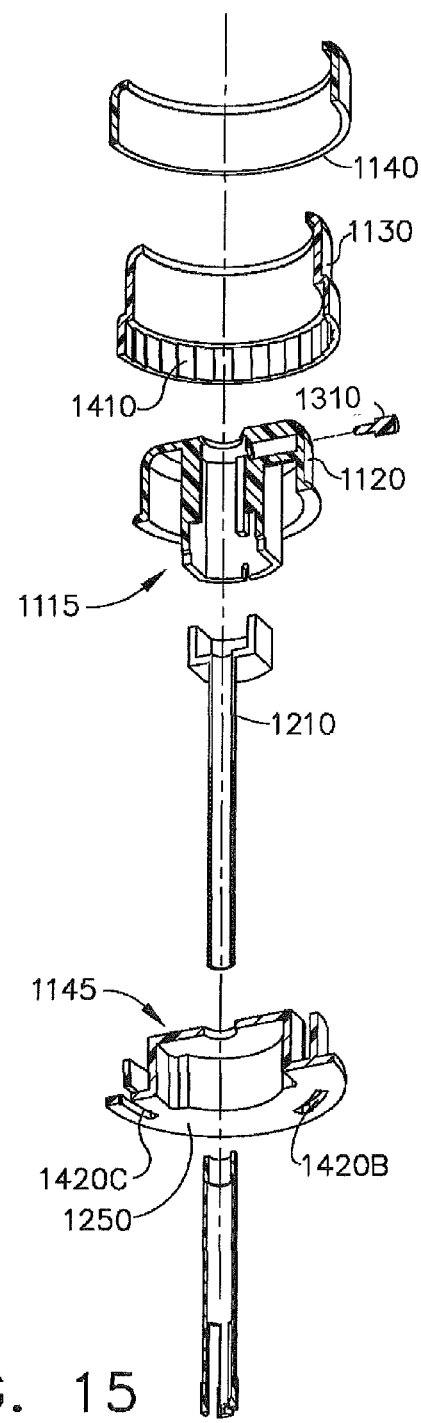
FIG. 15 is a partial cross sectional view of the FIG. 14 components.

Referring now to FIGS. 14 and 15, housing 1130, in one expression, is provided with a toothed distal medial surface 1410. When housing 1115 is assembled, toothed surface 1410 engages pawls 1420A, 1420B, 1420C. When housing 1130 is rotated, pawls 1420 permit rotation in a single direction creating a slip clutch arrangement. Rotation of housing 1130 in turn rotates housing 1120 which in turn rotates proximal obturator tube 1210.

Figure 16:
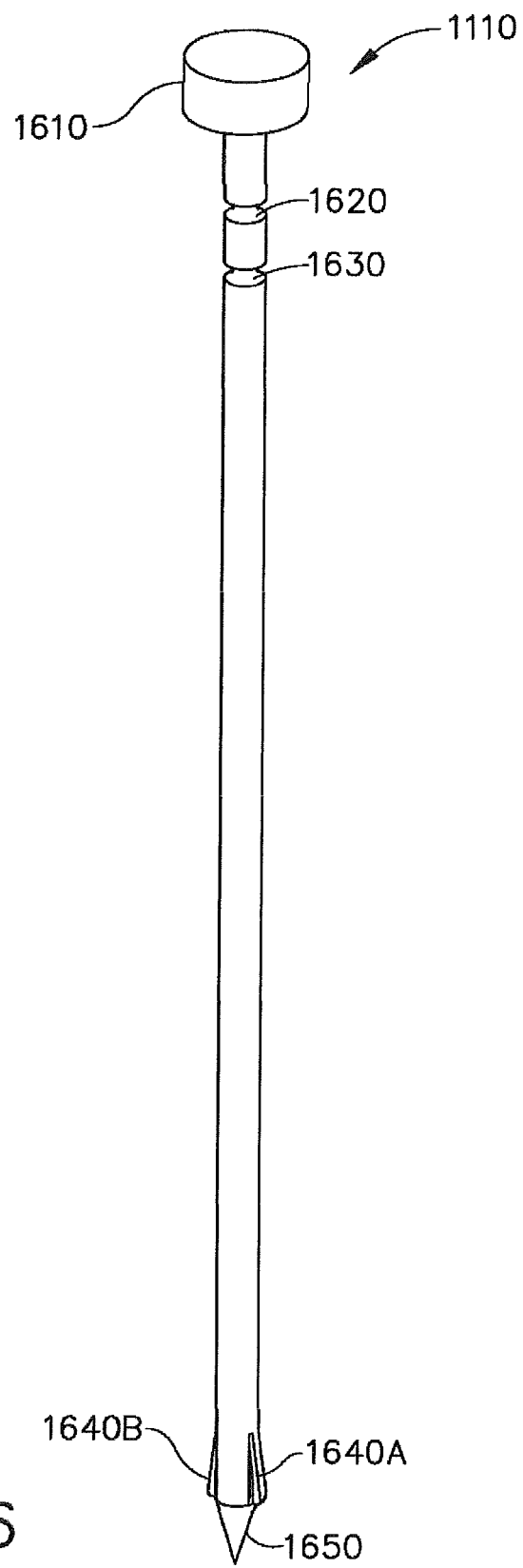
FIG. 16 is an isometric view of an obturator shaft for use with the FIG. 11 trocar.

Obturator 1115 is provided with obturator shaft 1110 as shown in FIG. 16. Shaft 1110 is provided with a gripping surface 1610 and detents 1620 and 1630. The distal end of shaft 1110 is provided with leaf spring anchor extension fingers 1640A and 1640B adapted to engage a medial flange portion of anchor 1170. Shaft tip 1650 is provided at the distal end of shaft 1110 and may be an optical tip, a bladed tip, a blunt tip or any other tip known in the art.

FIG. 17 illustrates cannula 1105 of trocar 1100. In one expression of trocar 1100, cannula 1105 is comprised of a housing 1710, a proximal cannula tube 1160, a distal cannula tube 1180 located adjacent tube 1160 and an anchor 1170 which may be located at a distal end of tube 1180. Anchor 1170, in one expression, is provided with proximal ring 1730 and distal ring 1720 and living hinges 1740. Living hinges 1740 may be biased to an open position as shown in FIG. 17. Distal ring 1720 includes a medial annular flange adapted to engage fingers 1640A and 1640B of obturator shaft 1110 to facilitate collapsing the anchor 1170 for insertion into an anatomic structure. As depicted in FIG. 17, distal tube 1180 is provided with a corrugated surface which may reduce friction forces during cannula tube 1180 retraction into cannula tube 1160. When cannula tube 1180 is retracted into tube 1160, tube 1180 is held in place through an interference fit provided by the reduced proximal diameter of tube 1160, as is shown in FIG. 18. Housing 1710 may be provided with a sealing system 1820 and 1830 to prevent the escape of insufflatory gas where the seal 1820 is a duckbill valve and 1830 is a diaphragm seal. Any form of seal may be used to prevent the escape of insufflatory gas, as is known and understood in the art. Cannula 1105 is provided with chamfered opening 1830 to facilitate insertion of obturator shaft 1110 as well as surgical instruments.

Figure 19:
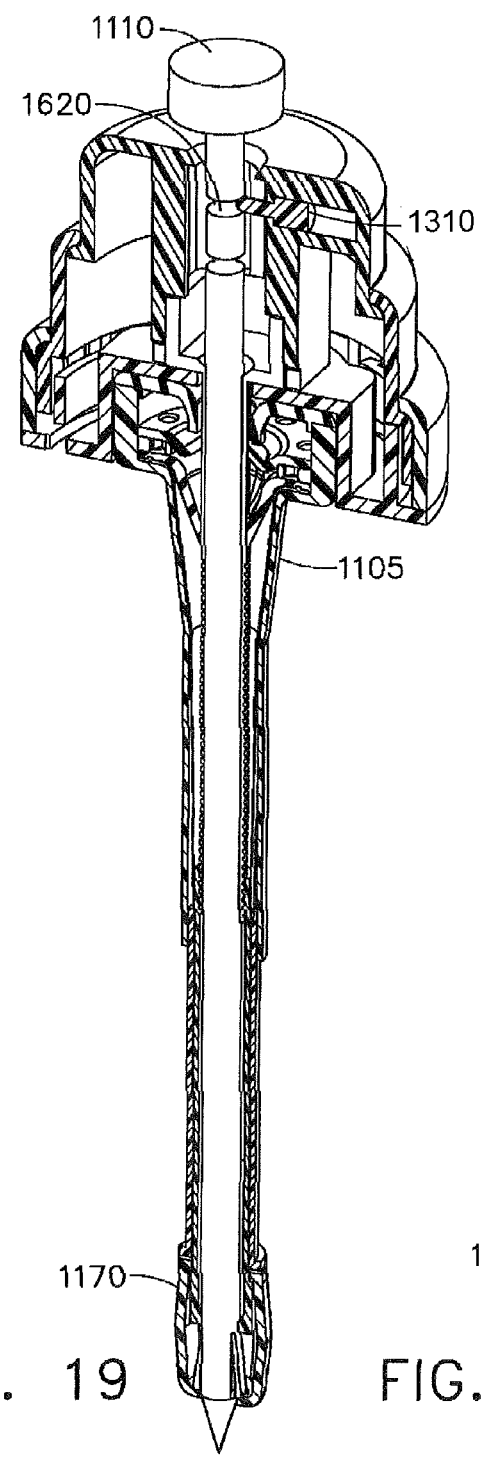
FIG. 19 is a partial cross-sectional view of the obturator depicted in FIG. 16 inserted into the cannula depicted in FIG. 17 prior to insertion into an operative site.
Figure 20:
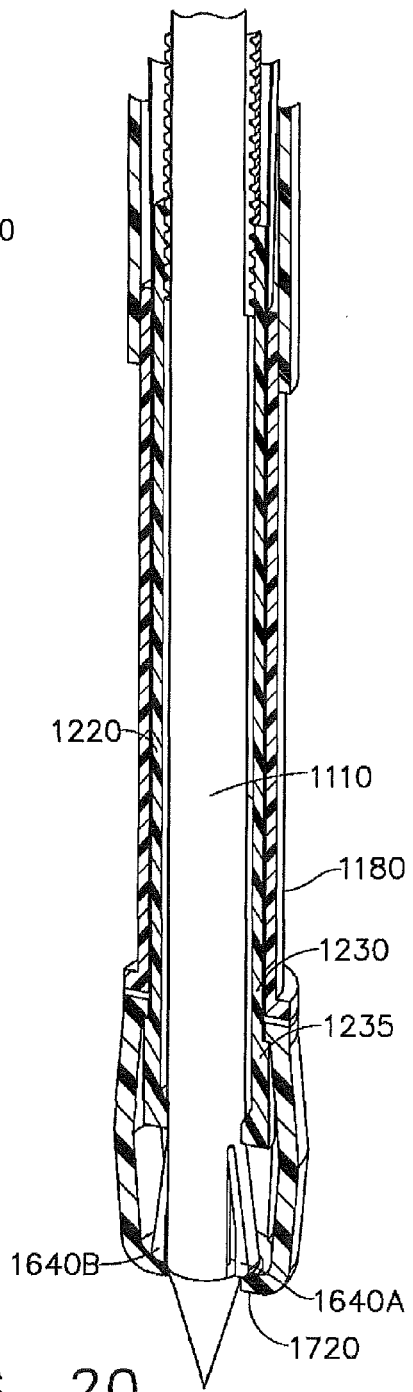
FIG. 20 is a close up of the cannula tube and obturator depicted in FIG. 19.

FIG. 19 depicts a partial cross sectional view of trocar 1100 with obturator shaft 1110 inserted through obturator housing 1115 and obturator shaft detent 1620 engaged with detent pin 1310. In this position, anchor extension fingers 1640A and 1640B engage anchor ring 1720 (see FIG. 20) and push anchor 1170 distally collapsing anchor 1170 about tube 1180. In this position, trocar 1100 is armed for insertion into an anatomic structure. Referring to FIG. 20, obturator shaft 1110 engages distal tube locking fingers 1310 biasing fingers 1310 laterally. In this biased position, locking fingers 1310 radial teeth 1235 engage anchor proximal ring 1730 permitting axial force transfer from obturator shaft 1110 to cannula distal tube 1180.

Figures 21, 22:
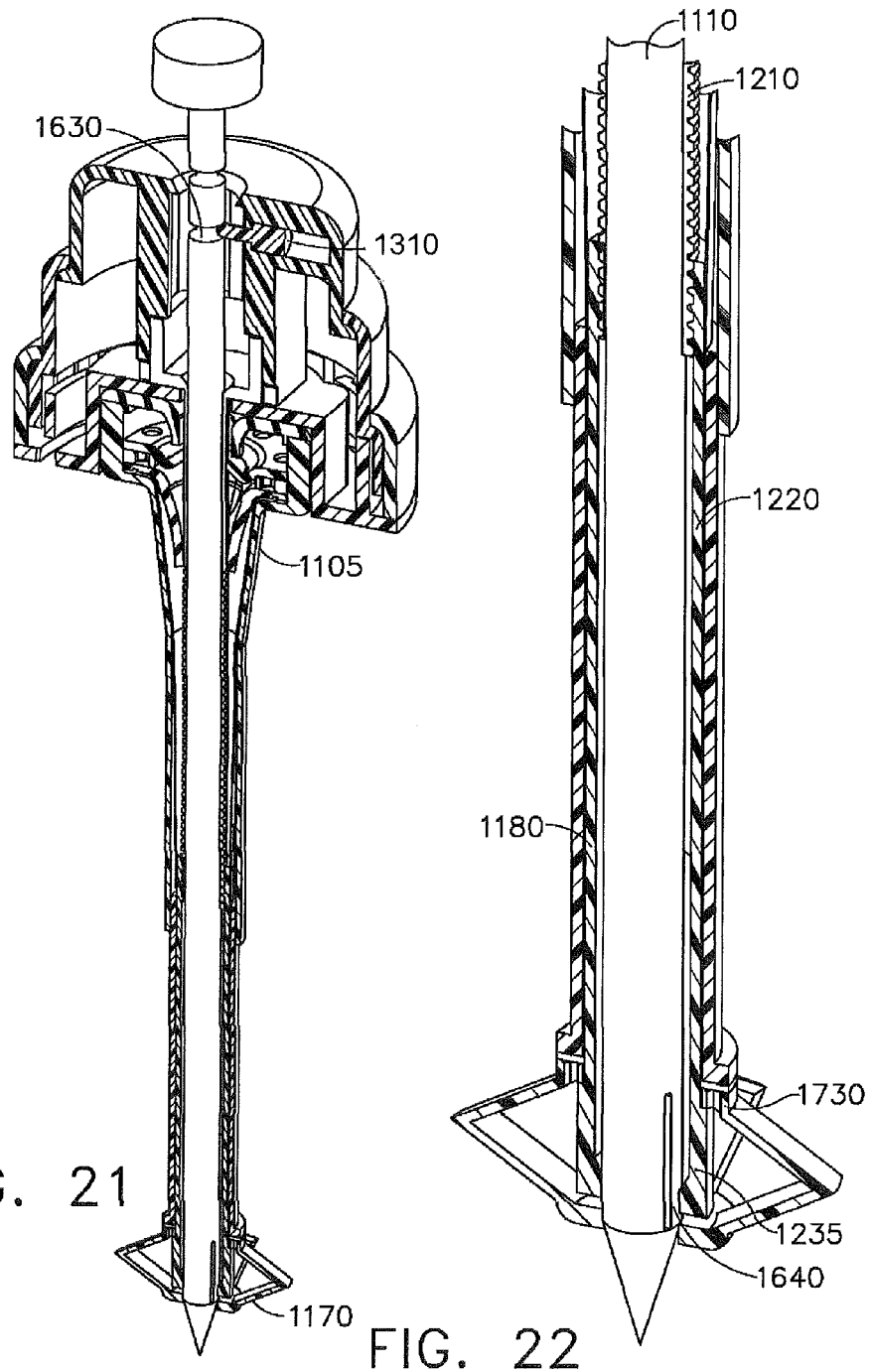
FIG. 21 is a partial cross-sectional view of the FIG. 19 assembly with the obturator shaft moved to the anchor deployment detent and the cannula anchors in a deployed state.
FIG. 22 is a close up view of the FIG. 21 anchor and distal end of the obturator.

Once inserted into an anatomic structure, it may be desirable to deploy anchor 1170 as shown in FIGS. 21 and 22. Applying proximal axial force on obturator shaft 1110 moves shaft 1110 detent 1620 out of engagement with pin 1230 and into engagement with detent 1630. This movement removes fingers 1640A and 1640B from engagement with anchor ring 1720 permitting anchor 1170 to bias to a deployed state. In this state, anchor 1170 may engage the interior wall of an anatomic structure, preventing inadvertent removal of cannula 1105 during surgical instrument exchanges.

It may be desirable to reduce the overall length of cannula 1105. Cannula 1105 length change may be accomplished in vivo or ex vivo, with the anchor 1170 in a collapsed state or deployed state. With obturator shaft 1110 inserted into obturator housing 1115 such that shaft detents 1620 or 1630 engage pin 1230, shaft 1110 engages locking fingers 1230 such that shaft 1110 and tube 1220 create an interlocking fit, or may couple in a locking fashion, and pin 1230 and detents 1620 or 1630 create an interference fit. This interference fit permits transfer of force from housing 1120 to shaft 1220. Similarly, engagement of toothed surface 1410 and pawls 1420A, 1420B, and 1420C permits the transfer of force (e.g. rotational force) applied to housing 1130 to tube 1210. When housing 1130 is rotated and housing 1120 is held in a stationary position, threads on lateral surface of tube 1210 engage threads on medial surface of 1220, rotating tube 1210 and thereby driving tube 1220 in a proximal direction. Radial teeth 1235 engage anchor ring 1730 transferring proximal axial force from tube 1220 to cannula tube 1180 thereby moving cannnula tube 1180 in a proximal direction into tube 1160, shortening the length of cannula 1105. Cannula tube 1180 is held in position due to the friction between tube 1160 and 1180, as stated previously. Once a desired length is achieved, obturator shaft 1110 is removed as shown in FIG. 23.

Upon shaft 1110 removal, locking fingers 1230 return to a medially biased position as shown in FIG. 24. In this position, radial teeth 1235 disengage from ring 1730 permitting removal of obturator 1115 from cannula 1105. As shown in FIGS. 23 and 24, cannula tube 1180 is fully withdrawn into tube 1160. It is understood that tube 1180 may be withdrawn partially into tube 1160 as well.

Figures 25, 26:
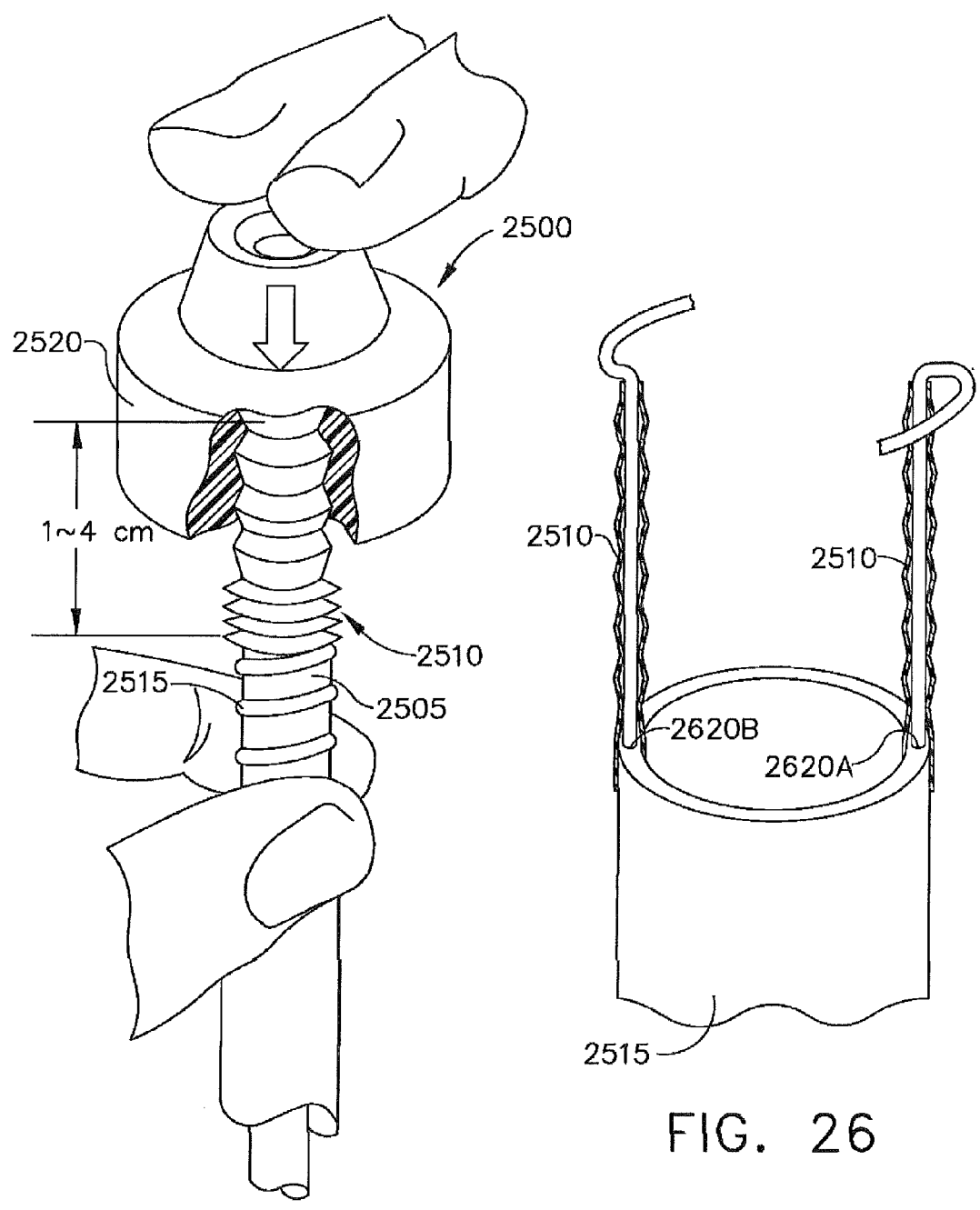

Referring now to FIG. 25, another expression of a surgical trocar is depicted. Trocar 2500 includes a collapsible segment 2510 which may be useful in making preliminary adjustments to overall cannula 2505 length. Segment 2510 is located adjacent cannula tube 2515 and cannula housing 2520. Before inserting a trocar into an anatomic structure, it may be desirable to approximate cannula length which may reduce time taken to adjust cannula length in vivo. As depicted in FIG. 25, preliminary adjustment may be achieved by an accordion section 2510 which may be comprised of an elastomer and be flexible in nature, or may be rigid, depending upon application and need.

One expression of collapsible segment 2510 adjustment mechanism depicted in FIG. 25 is shown in FIGS. 26, 26A and 26B. Tension members 2620A and 2620B are affixed to cannula tube 2515 at tension members 2620A and 2620B distal ends. Proximal ends of members 2620A and 2620B are affixed to spool 2630. Spool 2630 includes a keyseat 2640 adapted to receive obturator 2650 key 2655. Rotation of obturator 2650 transfers rotational force through key 2655 to keyseat 2640 thereby turning spool 2630 and winding tension members 2620A and 2620B around spool 2640. This winding shortens tension members 2620A and 2620B collapsing section 2510. As depicted in FIG. 26, section 2510 is an accordion type housing having lateral and medial surfaces with tension members 2620A and 2620B located in a plane between lateral and medial section 2510 segments. Members 2620A and 2620B may be located on a medial surface or a lateral surface depending upon application and need.

Cannula housing 2520 lateral surface, in one expression, is provided with a lock 2660 adapted to hold spool 2630 in a fixed position relative to housing 2520. Lock 2660 may be a camming lock where annular movement drives a portion of lock medially onto a lateral surface of spool 2630 holding spool 2630 and housing 2520 stationary relative to each other.

Referring now to FIGS. 27A, 27B, 27C, 27D, and 27E, a trocar insertion handle 2700 is provided. Handle 2700 is adapted to receive a surgical trocar 2740. Handle 2700 is further provided with an obturator 2720. Obturator 2720 is adapted to receive and engage cannula 2740. Anchor deployment button 2710 is provided at a proximal end of obturator 2720 and is adapted to cooperate with anchor 2770 located at cannula 2740 distal end. When button 2710 is depressed distally, spring 2730 is collapsed between button 2710 and handle housing 2705, anchor 2770 is moved distally, collapsing anchor 2770 around cannula 2740 placing trocar 2740 in an armed state, ready for insertion into an anatomic structure. Obturator 2720 is provided with a detent in communication with lever lock 2775 to hold anchor 2770 in a collapsed state (not shown). Obturator 2720 may be provided with a tip 2750 suitable for insertion through an anatomic structure (e.g. abdominal wall, etc.).

Figures 27A, 27B:
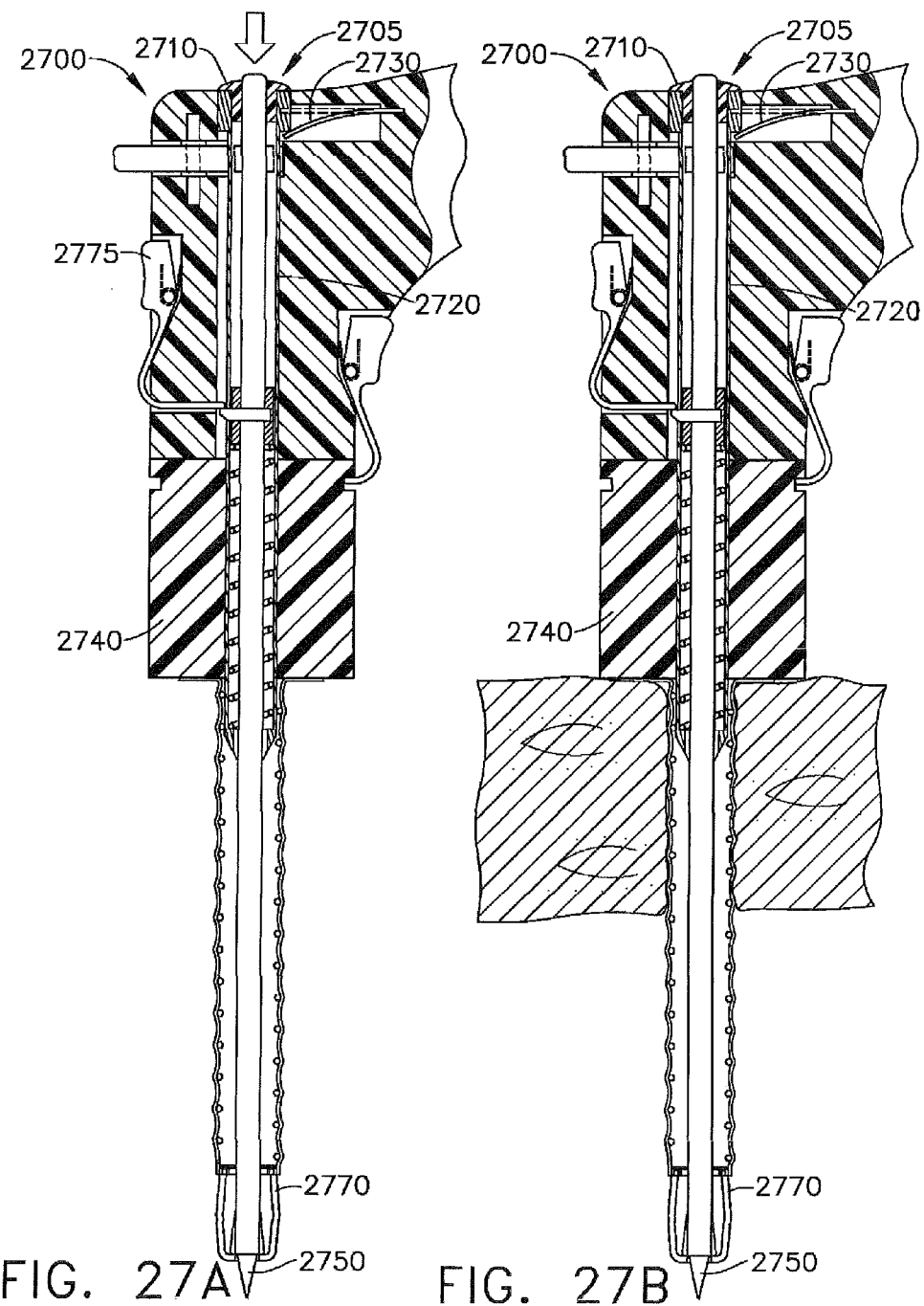
FIGS. 27A, 27B, 27C, 27D, and 27E depict a mechanical deployment apparatus for a trocar having an in vivo anchor assembly.
Figures 27C, 27D:
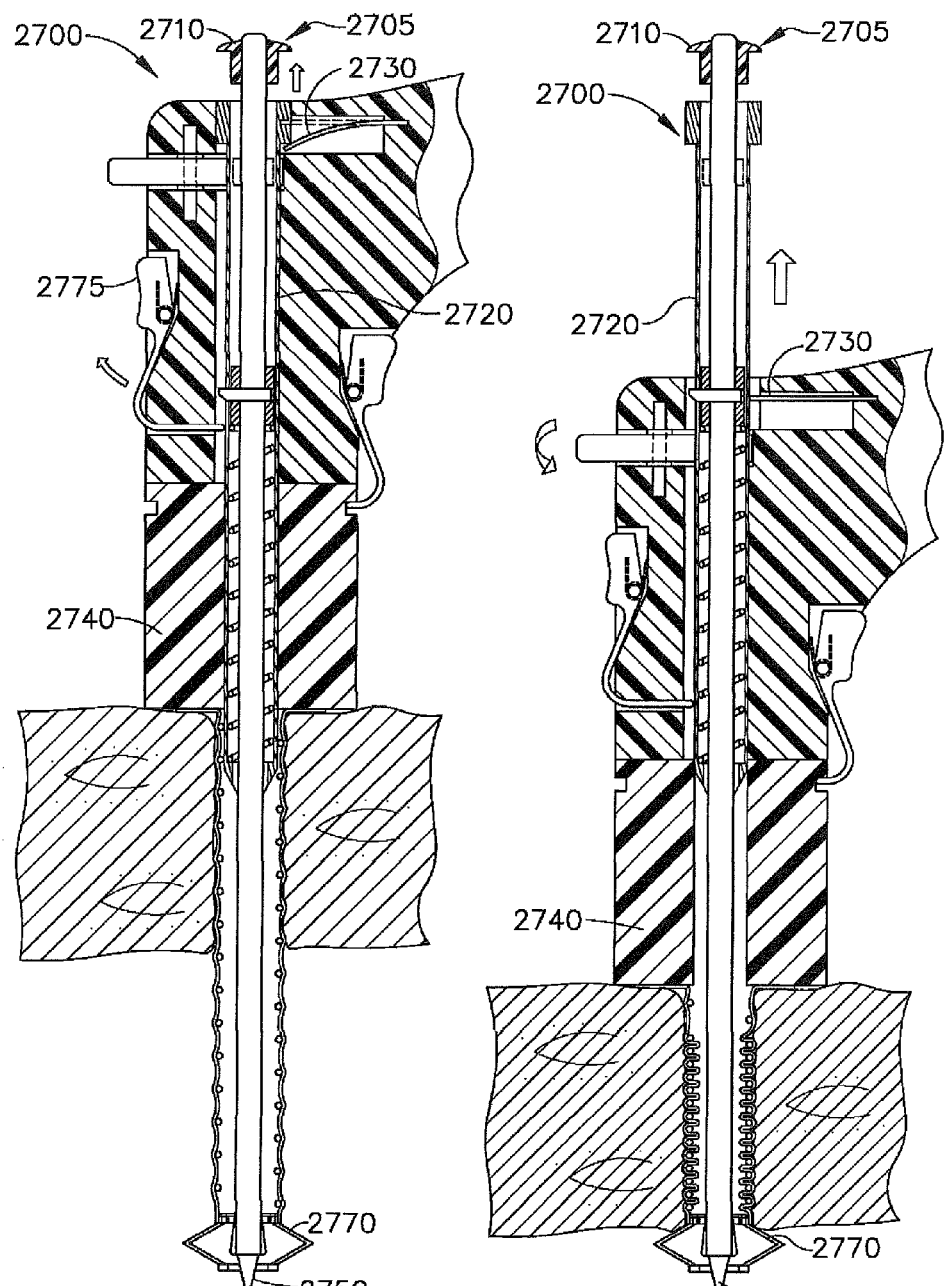
Figure 27E:
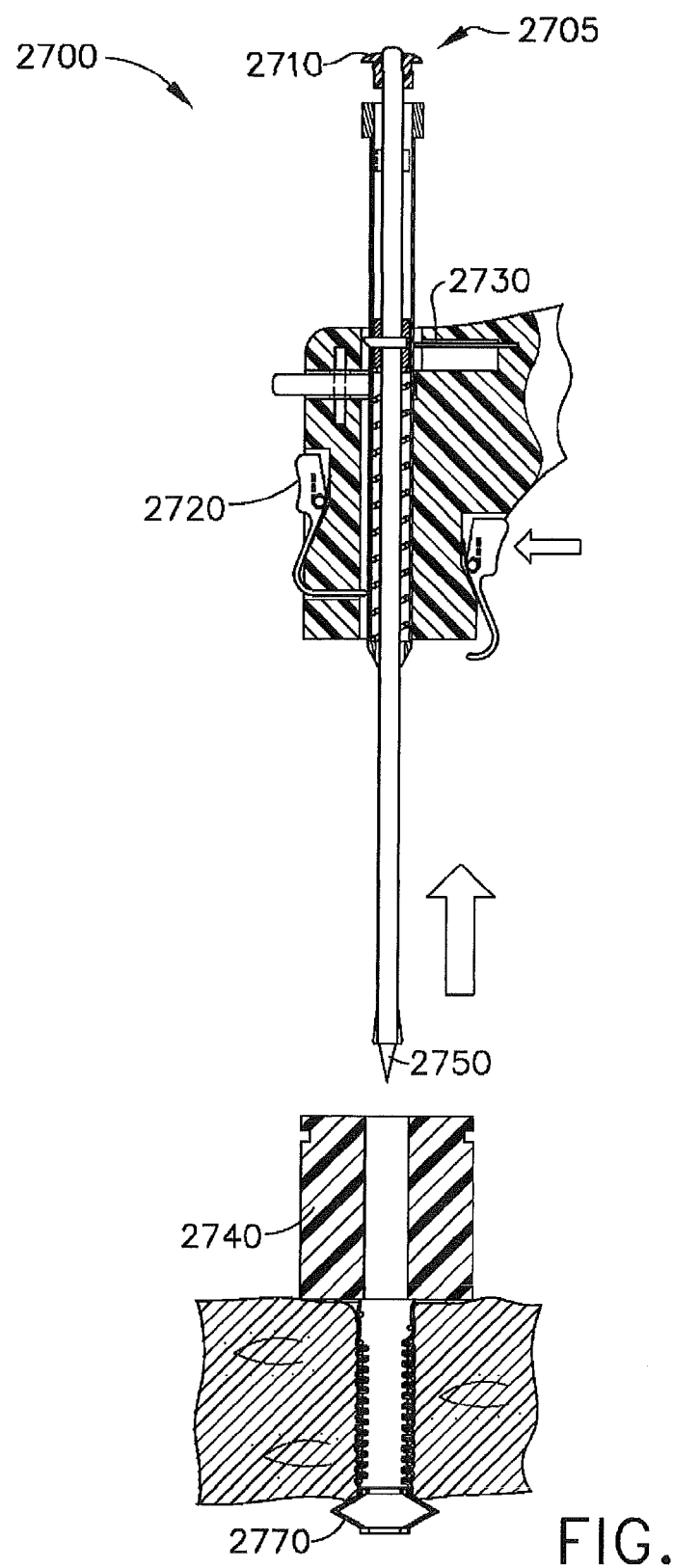

After insertion of trocar 2740 into an anatomic structure as shown in FIG. 27B, it may be desirable to deploy anchor 2770. Button 2775 is depressed allowing spring 2730 to bias obturator 2720 proximally, permitting anchor 2770 to assume a deployed state. Depending upon the composition of anchor 2770, it may be necessary to pull obturator button 2710 proximally to deploy anchor 2770. Once anchor 2770 is deployed, handle 2700 may be removed as shown in FIG. 27D. As shown, handle 2700 and obturator 2720 are of unitary construction. It is contemplated that handle 2700 and obturator 2720 may comprise two or more separate components. Upon removal of handle 2700, cannula 2740 may be shortened to an appropriate length. It is also contemplated that handle 2700 may further comprise a cannula adjustment mechanism such that cannula adjustment is accomplished with handle 2700 attached to cannula 2740.

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. Accordingly, the scope of the present invention should be considered in terms of the following claims and is understood not to be limited to the details of structure, materials, or acts shown and described in the specification and drawings.

The invention claimed is:

1. A surgical access device comprising:
   a) a distal cannula tube; a proximal cannula tube;
   b) an anchor adjacent the distal cannula tube;
   c) a first obturator housing and a second obturator housing located proximal to the proximal cannula tube; a first obturator tube attached to the first housing; a second obturator tube adjacent the first obturator tube, the second obturator tube having a lock to engage the distal cannula tube, the obturator tubes located within the distal and proximal cannula tubes;

d) an obturator shaft removably placed within the first obturator tube and second obturator tube, the obturator shaft detachedly connected to the second housing, the shaft having a leaf spring to engage the anchor; and e) a pin fixedly attached within the second housing.

2. The surgical access device of claim 1, wherein the obturator shaft has a detent that engages the pin.

3. The surgical access device of claim 2, wherein the anchor is biased to a deployed state.

4. The surgical access device of claim 3, wherein distal linear movement of the obturator shaft to a first position moves the anchor from a deployed state to a collapsed state.

5. The surgical access device of claim 3, wherein the anchor is comprised of at least two living hinges.

6. The surgical access device of claim 4, wherein proximal linear movement of the obturator shaft to a second position deploys the anchor and engages the second obturator tube.

7. The surgical access device of claim 6, further comprising a raised helical surface on the first obturator tube engaging a helical impression on the medial surface of the second obturator tube wherein rotation of the second obturator housing relative to the first obturator housing causes the second obturator tube to engage the first obturator tube driving the second obturator tube proximally over the first obturator tube thereby driving the distal cannula tube proximally.

8. The surgical access device of claim 7, wherein the distal cannula tube lateral surface is corrugated.

9. The surgical access device of claim 7, wherein the distal cannula tube telescopes into the proximal cannula tube.

10. A surgical access device comprising:
   a) a cannula housing;
   b) a distal cannula tube; a proximal cannula tube attached to the cannula housing;
   b) an anchor disposed about the distal cannula tube;
   c) a first obturator housing and a second obturator housing located proximal to the cannula housing; a first obturator tube attached to the first housing; a second obturator tube adjacent the first obturator tube, the second obturator tube having a lock to engage the distal cannula tube, the obturator tubes located within the distal and proximal cannula tubes; the cannula housing nested within the first obturator housing;
   d) a pin fixedly attached within the second housing; and
   d) an obturator shaft removably placed within the first obturator tube and second obturator tube, the obturator shaft detachedly connected to the second housing, the shaft having a finger to engage the anchor.

11. The surgical access device of claim 10, wherein the obturator shaft has a detent that engages the pin.

12. The surgical access device of claim 11, wherein the anchor is biased to a deployed state.

13. The surgical access device of claim 12, wherein distal linear movement of the obturator shaft to a first position moves the anchor from a deployed state to a collapsed state.

14. The surgical access device of claim 13, wherein proximal linear movement of the obturator shaft to a second position deploys the anchor and engages the second obturator tube.

15. The surgical access device of claim 14, further comprising a raised helical surface on the first obturator tube engaging a helical impression on the medial surface of the second obturator tube wherein rotation of the second obturator housing relative to the first obturator housing causes the second obturator tube to engage the first obturator tube driving the second obturator tube proximally over the first obturator tube thereby driving the distal cannula tube proximally.

16. A surgical access device comprising:
   a) a cannula housing having a valve located therein;
   b) a distal cannula tube; a proximal cannula tube attached to the cannula housing;
   b) an anchor disposed about the distal cannula tube, the anchor comprised of at least two living hinges;
   c) a first obturator housing and a second obturator housing located proximal to the cannula housing; a first obturator tube attached to the first housing having a raised helical surface; a second obturator tube adjacent the first obturator tube, the second obturator tube having a tooth to engage the distal cannula tube and a pin located within the second obturator housing; a helical impression on the second obturator tube medial surface engaging the raised helical surface; the obturator tubes located within the distal and proximal cannula tubes; the cannula housing nested within the first obturator housing; and
   d) an obturator shaft removably placed within the first obturator tube and second obturator tube, the obturator shaft detachedly connected to the second housing, the shaft having a finger to engage the anchor and a detent to engage the pin.

17. The surgical access device of claim 16, wherein the anchor is biased to a deployed state.

* * * * *